(12) United States Patent
Ascenzi

(10) Patent No.: US 7,124,067 B2
(45) Date of Patent: Oct. 17, 2006

(54) SYSTEM AND METHOD FOR MODELING BONE STRUCTURE

(76) Inventor: Maria-Grazia Ascenzi, 1713 Bryn Mawr Ave., Los Angeles, CA (US) 90405

(*) Notice: Subject to any disclaimer, the term of this patent is extended or adjusted under 35 U.S.C. 154(b) by 620 days.

(21) Appl. No.: 09/981,684

(22) Filed: Oct. 17, 2001

(65) Prior Publication Data

US 2002/0082779 A1 Jun. 27, 2002

Related U.S. Application Data

(60) Provisional application No. 60/240,884, filed on Oct. 17, 2000, provisional application No. 60/246,198, filed on Nov. 6, 2000.

(51) Int. Cl.
*G06F 9/455* (2006.01)

(52) U.S. Cl. .................. 703/11; 600/449; 600/586; 623/23.51; 623/23.56

(58) Field of Classification Search ................ 703/11, 703/2; 424/9.2, 49; 382/128; 600/586, 600/449, 36; 514/12; 623/23.51, 23.56
See application file for complete search history.

(56) References Cited

U.S. PATENT DOCUMENTS

| | | | |
|---|---|---|---|
| 5,732,469 A | | 3/1998 | Hamamoto et al. |
| 5,947,893 A | * | 9/1999 | Agrawal et al. .............. 600/36 |
| 6,083,264 A | * | 7/2000 | Wood et al. ............. 623/23.56 |
| 6,213,958 B1 | * | 4/2001 | Winder ....................... 600/586 |
| 6,293,970 B1 | | 9/2001 | Wolfinbarger, Jr. et al. |
| 6,333,313 B1 | * | 12/2001 | Copland, III et al. ......... 514/12 |
| 6,416,737 B1 | * | 7/2002 | Manolagas et al. .......... 424/9.2 |
| 6,442,287 B1 | * | 8/2002 | Jiang et al. ................. 382/128 |
| 6,517,487 B1 | * | 2/2003 | Mazess et al. .............. 600/449 |
| 6,692,532 B1 | * | 2/2004 | Healy et al. ............. 623/23.51 |
| 2002/0136696 A1 | * | 9/2002 | Lee et al. ...................... 424/49 |

FOREIGN PATENT DOCUMENTS

WO WO-02/33679 A2 4/2002
WO WO-02/060347 A2 8/2002

OTHER PUBLICATIONS

R. Lakes, "Materials with Structural hieracrchy", Nature 361, Feb. 1993.*
Aoubiza et al. (1996) "On the mechanical characterization of compact bone structure using homogeneization theory", *J. Biomech.* 29:1539-1547.
Ascenzi, A. et al., (1965) An electron microscope study of osteon calcification. J. Ultr. Research., 12, 287-303.
Boivin et al., (2000) "Alendronate Increases Bone Strength by Increasing the Mean Degree of Mineralization of Bone Tissue in Osteoporotic Women", *Bone*, 27:687-694.
Bonucci, E. (2000) Basic composition and structure of bone. In: Mechanical testing of bone (An Y. and Draughn R. eds), CRC Press, Boca Raton, Florida, p. 3-21.

(Continued)

*Primary Examiner*—Paul L. Rodriguez
*Assistant Examiner*—Kandasamy Thangavelu
(74) *Attorney, Agent, or Firm*—Darby & Darby

(57) ABSTRACT

The present invention discloses a structural and mechanical model and modeling methods for human bone based on bone's hierarchical structure and on its hierarchical mechanical behavior. The model allows for the assessment of bone deformations, computation of strains and stresses due to the specific forces acting on bone during function, and contemplates forces that do or do not cause viscous effects and forces that cause either elastic or plastic bone deformations.

50 Claims, 21 Drawing Sheets

OTHER PUBLICATIONS

Borah et al., (2002) "Risedronate Preserves Trabecular Architecture and Increases Bone Strength in Vertebra of Ovariectomized Minipigs as Measured by Three-Dimensional Microcomputed Tomography", *Journal of Bone and Mineral Research*, 17:1139-1147.
Bouxsein M. (2003) "Bone quality: where do we go from here?", *Osteoporos Int.*, 14(suppl 5):S118-S127.
Boyde A, Hobdell M H (1969) Scanning electron microscopy of lamellar bone. Z. Zellforsch 93, 213-231.
Burr and Hooser (1995) "Alterations to the En Bloc Basic Fuchsin Staining Protocol for the Demonstration of Microdamage Produced In Vivo", *Bone*, 17:431-433.
Carter D. and Hays W C (1977) The compressive behavior of bone as a two-phase porous structure. J. Bone Joint Surg. 59, 954-962.
Cowin, SC (1999) Bone poroelasticity. J. Biomech. 32, 217-238.
Dufresne et al., (2003) "Risedronate Preserves Bone Architecture in Early Postmenopausal Women In 1 Year as Measured by Three-Dimensional Microcomputed Tomography", *Calcified Tissue International*, Springer-Verlag 2003 (electronic publication).
Engström A, Engfeldt B (1953) Lamellar structure of osteons demonstrated by microradiography. Experientia 9, 19.
Frasca, P., Harper, R. and Katz, J. (1976) Isolation of single ostesons and osteons lamellae. Acta Anat., 95, 122-129.
Hogan H A (1992) Micromechanics modeling of Haversian cortical bone properties. J. Biomech. 25, 549-556.
Katz J L (1981) Composite material models for cortical bone. In Mechanical Properties of Bone (Edited by Cowin, SC), AMD, 45, 171-184. American Society of Mechanical Engineers, New York.
Kölliker A (1854) Manual of Man Microscopical Anatomy. Lippincott, Grambo and Co., Philadelphia.
van Leeuwenhoek A (1693) An extract of a letter from Mr. Anth. Van. Leeuwenhoek containing several observations on the texture of the bones of animals compared with that of wood: on the bark of trees: on the little scales found on the cuticula, etc. Philos. Trans. R. Soc. London 202, 838-843.
Marotti G (1979) Osteocyte orientation in human lamellar bone and its relevance to the morphometry of periosteocytic lacunae. Metab. Bone Dis & Rel. Res. 1, 325-333.
Martin B.M. (2003) "Fatigue Microdamage as an Essential Element of Bone Mechanics and Biology", *Calcif Tissue International*, 73:101-107.
Michel, M. et al. (1993) Compressive fatigue behavior of bovine trabecular bone. J. Biomech, 26, 453-463.
Mori et al., (1997) "Trabecular Bone Volume and Microdamage Accumulation in the Femoral Heads of Women With and Without Femoral Neck Fractures", *Bone*, 21:521-526.
Reid S A (1986) A study of lamellar organization in juvenile and adult human bone. Anat. Embryol. 174, 329-338.
Saatcioglu, M. (1991) Modeling hysteretic force-deformation relationship for reinforced concrete elements. In: Earthquake-Resistant Concrete Structures, Inelastic Response and Design (S.K. Ghosh, ed.), American Concrete Institute (ACI-SP 127), Detroit, 153-198.
Schaffler, M.B. et al. (1990) Long-term fatigue behavior of compact bone at low strain magnitude and rate. Bone, 11, 321-326.
Schaffler et al., (1995) "Aging and Matrix Microdamage Accumulation in Human Compact Bone", *Bone*, 17:521-525.
Seireg, A. and Kempke, W. (1969) Behavior of in vivo bone under cyclic loading. J. Biomech., 2, 455-461.
Sevostianov and Kachanov (2000) "Impact of the porous microstructure on the overall elastic properties of the osteonal cortical bone", *J. of Biomechanics*, 33:881-888.
Smith J W (1960) The arrangement of collagen bundles in human secondary osteons. J. Bone Joint Surg. 42B, 588-605.
Bouxsein ML (2003) Bone quality: an old concept revisited, Osteop Int, 14: S1-S2.
Boyde A (1984) Methodology of calcified tissue specimen preparation for SEM. In: Methods of Calcified Tissue Preparation, Dickson GR editor, Elsevier, Amsterdam, 251-307.
Boyde A: What happens to cracks in bone? In: Proceedings of Bioengineering in Ireland (8) and the 16th Meeting of the Northern Ireland Biomedical Engineering Society—Joint Conference 2002, Eds: FitzPatrick DP and McCormack BAO, Dublin: University College, 23.
Boyde A (2003) The real response of bone to exercise, J Anat, 203: 173-189.
Boyde A et al., (1983) Tandem scanning reflected light microscopy of internal features in whole bone and tooth samples, J Microsc, 132: 1-7.
Burr DB, Stafford T (1985) Validity of the bulk-staining technique to separate artifactual from in vivo fatigue microdamage, Clin. Ortho. And Related Research, 260:305-308.
Guo XE, et al., (1994) Finite Element Modeling of Damage Accumulation in Trabecular Bone Under Cyclic Loading, J Biomech, 27: 145-155.
Martin RB, Burr DB (1982) A hypothetical mechanism for the stimulation of osteonal remodeling by fatigue damage, J Biomech, 15, 137-139.
Pauwels (1948) "The Principles of Construction of the Locomotor System. Their Significance for the Stressing of the Tubular Bones", *Z. Anat. Entwickl. Gesch.*, 114:129-166.
Picard S et al., (2003) Micro-architectural strut analysis study on paediatric bone, Procedings of the 25thannual meeting of the American Society of Bone and Mineral Research 2003, Minneapolis.
Zioupos P. (2001) "Accumulation of *in-vivo*, fatigue microdamage and its relation to biomechanical properties in ageing human cortical bone", *J. of Microscopy*, 201:270-278.
Kino et al., (1995) "Intermediate Optics in Nipkow Disk Microscopes", *Handbook of Biological Confocal Microscopy*, ed. James B. Pawley, Plenum Press, New York, p. 155-165.
Marotti et al., (1994) "Structure and Function of Lamellar Bone", *Clinical rheumatology*, 13(suppl. 1):63-68.
Ascenzi, A. and A. Benvenuti, "Orientation of Collagen Fibers at the Boundary Between Two Successive Osteonic Lamellae and its Mechanical Interpretation". J. Biomechanics. 19(6):455-463 (1986).
Ascenzi, A. et al., "An Approach to the Mechanical Properties of Single Osteonic Lamellae". J. Biomechanics 6:227-235 (1973).
Ascenzi, et al., "Distribution of collagen bundle orientation in human secondary osteons", Scanning, vol. 26, 2 (2004), pp. 90-91.
Ament, Ch. and Hofer, E.P., (2000) A fuzzy logical model of fracture healing. Journal of Biomechanics, 32:961-968.
Amprino, R. and Engström, A. (1952) Studies on X-ray absorption and diffraction of bone tissue. Acta Anat , 15, 1-22.
Antman, S. (1995) Nonlinear Problems of Elasticity. Springer. New York.
Ascenzi, M.-G. (2000) National Science Foundation grant description.
Ascenzi, M.-G.. Benvenuti, A., and Ascenzi, A. (2000) Single osteon micromechanical testing. In: Mechanical testing of bone (An Y. and Draughn R. eds), CRC Press, Boca Raton, Florida.
Ascenzi, M.-G. (1999a) Evidence of macroscopic prestress in human femoral shaft, Abstracts of the XVIIth conference of the International Society of Biomechanics, Calgary.
Ascenzi, M.-G. (1999b) A first estimation of prestress in so-called circularly fibered osteonic lamellae, J. Biomech., 32, 935.
Ascenzi, M.-G. (1998a) A first estimate of prestress in so-called circularly fibered osteonic lamellae, Abstracts of the 11th conference of the European Society of Biomechanics, J. Biomech., 31, Suppl. I, 22.
Ascenzi, A., Benvenuti, A., Bigi, A., Foresti, E., Koch, M.H.J., Mango, F., Ripamonti, A., and Roveri, N. (1998) X-ray diffraction on cyclically loaded osteons. Calc. Tissue Int., 62:266-273.
Ascenzi, A., Ascenzi M. G., Benvenuti, A., and Mango, F. (1997) Pinching in longitudinal and alternate osteons during cyclic loading. J. Biomechanics, 30, 689-695.
Ascenzi, A., Baschieri P., and Benvenuti, A. (1994) The torsional properties of single selected osteons. J. Biomech., 27, 875-884.
Ascenzi, A., Baschieri P., and Benvenuti, A. (1990) The bending properties of single osteons. J. Biomech., 23, 763-771.
Ascenzi, A. (1988) The micromechanics versus the macromechanics of cortical bone—A comprehensive presentation. J. Biomech. Eng., 110, 357-363.

Ascenzi, A., Boyde, A., Portigliatti-Barbos, M. and Carando, S. (1987a) Micro-biomechanics vs Macrobiomechanics in cortical bone. A micromechanical investigation of femurs deformed by bending. J. Biomech., 20, 1045-1053.

Ascenzi, A., et al., (1986) Relationship between mechanical properties and structure in Secondary bone, Connective Tissue Research, 15:73-76.

Ascenzi, A., Benvenuti, A., Mango, F. and Simili, R. (1985) Mechanical hysteresis loops from single osteons: Technical devices and preliminary results, J. Biomech., 18, 391-398.

Ascenzi, A. and Bonucci, E. (1972) The shearing properties of single osteons. Anat. Rec., 172, 499-510.

Ascenzi, A. and Bonucci, E. (1968) The compressive properties of single osteons. Anat. Rec., 161, 377-392.

Ascenzi, A. and Bonucci, E. (1967) The tensile properties of single osteons. Anat. Rec., 158, 375-386.

Ascenzi, A., et al., (1967) An Electron Microscope Study on Primary Periosteal Bone. J. Ultr. Research, 18:605-618.

Ascenzi, A. and Bell, G.H., (1956) Bone as a mechanical engineering problem. In: The Biochemistry and Physiology of Bone (Bourne G. H. ed) Academic Press, New York.

Boyde, A., Bianco, P., Portigliatti-Barbos, M. and Ascenzi, A. (1984) Collagen Orientation in compact bone: 1. A new method for the determination of the proportion of collagen parallel to the plane of compact bone sections, Metab. Bone Dis. & Rel. Res., 5, 299-307.

Burr, D.B., Schaffler, M.B. and Frederickson, R.G. (1988) Composition of the cement line and its possible mechanical role as a local interface in human compact bone. J. Biomech., 21, 939-945.

Caler, W.E. and Carter, D.R. (1989) Bone creep-fatigue damage accumulation. J. Biomech., 22, 625-635.

Carter, D.R., Caler, W.E., Spengler, D. M., and Frankel, V. H. (1981), Fatigue behavior of adult cortical bone: The influence of mean strin and strain range., Acta Orthop. Scand., 52, 481-490.

Carter, D.R. and Spengler, D.M. (1978) Mechanical properties and composition of cortical bone. Clin. Orthop., 135, 192-217.

Carter, D.R. and Hayes, W.C. (1977) Compact bone fatigue damage—I. Residual strength and stiffness. J. Biomech., 10, 325-337.

Carter, D.R. and Hayes, W.C. (1976) Fatigue life of compact bone—I. Effects of stress amplitude, temperature and density. J. Biomech., 9, 27-34.

Carter, D.R., Hayes, W.C. and Schurman, D.J. (1976) Fatigue life of compact bone—II Effects of microstructure and density. J. Biomech., 9, 211-218.

Cook, J. and Gordon, J. E. (1964) A mechanism for the control of crack propagation in all brittle systems. Proc. R. Soc. Lond., Ser. A, 282, 508-520.

Couteau, B., Payan, Y., Lavallée, S. (2000) The mesh-matching algorithm: an automatic 3D mesh generator for finite element structures. J. Biomech., 33, 1005-1009.

Crolet J.-M., Aoubiza, B. and Meunier, A. (1993) Compact bone: numerical simulation of mechanical characteristics. J. Biomech., 26, 677-687.

Currey, J.D. (1964) Three analogies to explain the mechanical properties of bone. Biorheology, 2:1-10.

Currey, J.D. (1959) Differences in tensile strength of bone of different hystological types. J. Anat., 93, 87-95.

Evans, P. (1978) Relations between torsion properties and histology of adult human compact bone. J. Biomech., 11, 157-165.

Evans, F.G. and Vincentelli, R. (1969) Relation of collagen fiber orientation to some mechanical properties of human cortical bone. J. Biomech., 2, 63-71.

Frasca, P., Harper, R. and Katz, J. (1981) Strain and frequency dependence of shear storage modulus for human single osteons and cortical bone microsamples-size and hydration effects. J. Biomech, 14, 679-690.

Frasca, P., Harper, R. and Katz, J. (1977) Collagen fiber orientation in human secondary osteons. Acta Anat., 98, 1-13.

Giraud-Guille, M. M. (1988) Twisted plywood architecture of collagen fibrils in human compact bone osteons. Calc. Tissue Int., 42, 167-180.

Gupta, V., and Bergström, J.S. (1998) Compressive failure of rocks by shear faulting. J. of Geoph. Res. 103, 23, 875-23,895.

Hart, R.T., et al., (1992) Modeling the biomechanics of the mandible: a three-dimensional finite element study. J. Biomechanics, 25(3):261-286.

Hert J., Fiala P. and Petrtyl M. (1994) Osteon orientation of the diaphysis of the long bones in man. Bone, 15, 269-277.

Hayes, W. and Carter, D. (1979) Biomechanics of Bone. In: Skeleton Research: An Experimental Approach (D. Simmons and A. Kunin, eds.), Academic Press Inc., New York, 1, 263-299.

Höhling, H.J., Barckhaus, R.H., Krefting, E.R., Althoff, J. and Quint, P. (1990) Collagen mineralization: aspects of the structural relationship between collagen and apatite cristallites. In: Ultrastructure of Skeletal Tissues: Bone and Cartilage in Health and Disease (E. Bonucci and P.M. Morra, eds.), Kluwer Academic Publishers, Boston, 41-62.

Huja, S.S., Hasan, M.S., Pidaparti, R., Turner, C.H., Garetto, L.P. and Burr, D. (1999) Development of a fluorescent light technique for evaluating microdamage in done subjected to fatigue loading. J. Biomech., 32, 1243-1249.

Jepsen, K. J. and Davy, D.T. (1997) Comparison of damage accumulation measures in human cortical bone. J. Biomech., 30, 891-894.

Jepsen, K. J., Davy, D.T. and Krzypow, D. J. (1999) The role of the lamellar interface during torsional yielding of human cortical bone. J. Biomech., 32, 303-310.

Katz, J. L. and Meunier, A. (1987) The elastic anisotropy of bone. J. Biomech., 20, 1063-1070.

Katz, J. L. and Ukraincik, K. (1971) On the anisotropic elastic properties of hydroxyapatite. J. Biomech., 4, 221-227.

Kleerekoper, M., Villanueva, A. R., Stanciu, J., et al. (1985) The role of three-dimensional trabecular microstructure in the pathogenesis of vertebral compression fractures. Calc. Tissue. Int., 37, 594-597.

Koch, J. C. (1917) The laws of bone architecture. Am. J. Anat., 21, 177-293.

Lakes, R. (1995) On the torsional properties of single osteons, J. Biomech., 28, 1409-1410.

Mah, J. and Hatcher, D. (2000) Imagining trends and applications for the millenium. Orthod. Prod., 1, 14-18.

Martens, M., van Audekercke, R., de Meester, P. and Mulier, J. (1980) The mechanical characteristics of the long bones of the lower extremity in torsional loading. J. Biomech., 13, 667-676.

Miller, G. and Piotrowski, G. (1974) A brief note on the variability of the torsional strength of paired bones. J. Biomechanics, 7, 247-248.

Moreland, M. (1980) Morphological effects of torsion applied to growing bone. J. Bone Jt. Surg., 62-B, 230-237.

Philipson, B. (1965) Composition of cement lines in bone. J. Histochem. Cytochem., 13, 270-281.

Pidaparti, R. and Burr D. (1992) Collagen fiber orientation and geometry effects on the mechanical properties of secondary osteons. J. Biomech., 25, 869-880.

Piekarski, K. (1970) Fracture of bone . J. of Appl. Physics, 41, 215-223.

Portigliatti-Barbos, M., Bianco, P. and Ascenzi, A. (1983) Distribution of osteonic and interstitial components in the human femoral shaft with reference to structure, calcification, and mechanical properties. Acta Anat., 115, 178-186.

Portigliatti-Barbos, M., Bianco, P., Ascenzi, A. and Boyde, A. (1984) Collagen orientation in compact bone: II. Distribution of lamellae in the whole of the human femoral shaft with reference to its mechanical properties. Metab. Bone Dis. & Rel. Res., 5, 309-315.

Portigliatti-Barbos, M., Carando, S., Ascenzi, A. and Boyde, A. (1987) On the structural symmetry of human femurs, Bone, 8, 165-169.

Rho, J.Y., Zioupos, P., Currey, J.D., and Pharr ,G. M. (1999) Variations in the individual thick lamellar properties within osteons by nanoindentation, Bone, 25, 295-300.

Riggs, C. M., Lanyon, L. E., and Boyde, A. (1993a) Functional associations between collagen fibre orientation and locomotor strain direction in cortical bone of the equine radius, Anat. Embryol., 187, 231-238.

Riggs, C. M., Vaughan, L. C., Evans, G. P., Lanyon, L. E. and Boyde, A. (1993b) Mechanical implications of collagen fibre orientation in cortical bone of the equine radius, Anat. Embryol., 187, 239-248.

Sasaki N. (2000) Viscoelastic properties of bone and testing methods. In: Mechanical testing of bone (An Y. and Draughn R. eds), CRC Press, Boca Raton, Florida.

Schaffler, M., Burr, D. B. and Frederickson, R. G. (1987) Morphology of the osteonal cement line in human bone. Anat. Rec., 217, 223-228.

Shiga, T., Ogawa, J., Shibata, A. and Shibuya, J. (1970) The dynamic properties of reinforced concrete frames. Proceedings of the United States-Japan Seminar on Earthquake Engineering with emphasys on safety of school buildings. Sep., 346-363.

Simkin, A., and Robin,G. (1974) Fracture formation in differing collagen fiber pattern of compact bone. J. Biomech., 7, 183-188.

Vincentelli, R. and Evans, F. G. (1971) Relations among mechanical properties, collagen fibers, and calcification in adult human cortical bone. J. Biomech., 4, 193-201.

Ziv, V., Wagner, M. D., and Weiner, S. (1996) Microstructure-microhardness relations in parallel-fibered and lamellar bone. Bone, 18, 417-428.

Zysset, P.K., Guo X.E., Hoffler C.E., Moore K.E., and Goldstein S. (1999) Elastic modulus and hardness of cortical and trabecular bone lamellae measured by nanoindentation in the human femur. J. Biomech., 32, 1005-1012.

An, Y., et al., (2000) Basic Concepts of Mechanical Property Measurement and Bone Biomechanics. Mechancial Testing of bone and the Bone-Implant Interface, Chapter 2, pp. 23-40.

Ascenzi, A., and Boyde, A., (1993) Micromechanical aspects of normal and deformed cortical bone. In: Micromovement in Orthopaedics. A.R. Turner-Smith ed., Chapter 21, pp. 185-198. Oxford Medical Engineering Series 10, Medical Publications. Clarendon Press, Oxford.

Ascenzi, A., et al., (1987b) Distribution of Lamellae in Human Femoral Shafts Deformed by Bending with Interferences on Mechanical Properties. Bone, 8:319-325.

Ascenzi, A., and Benvenuti, A., (1980) Evidence of a state of initial stress in osteonic lamellae. Acta Orthop. Belg., 46:580-583.

Ascenzi, A., et al., (1965) The tensile properties of single osteons studied using a microwave extensimeter. In: Studies on the Anatomy and Function of Bone and Joints. F.G. Evans ed., pp. 121-141, Springer-Verlag, Berlin.

Carando, S., et al., (1991) Macroscopic shape of, and lamellar distribution within, the upper limb shafts, allowing interferences about mechanical properties. Bone, 12:265-269.

Carando, S., (1989) Orientation of collagen in human tibial and fibular shaft and possible correlation with mechanical properties. Bone, 10:139-142.

Currey, J.D. (1969) The relationship between the stiffness and the mineral content of bone. J. Biomechanics, 2:477-480.

Marotti, G., et al., (1994) Structure and function of lamellar bone. Clinical Rheumatology, 13(1):63-68.

McCutchen, C.W., (1975) Do mineral crystals stiffen bone by straitjacketing its collagen? J. Theor. Biol., 51:51-58.

Kotha et al., "*Tensile damage and its effects on cortical bone*", Journal of Biomechanics, 36 (2003) 1683-1689.

Kotha et al., "*Modeling the Tensile Mechanical Behavior of Bone along the Longitudinal Direction*", J. theor. Biol. (2002) 219, 269-279.

Biophysical Journal, vol. 79, Oct. 2000, 1737-1746, Ingomar Jager and Peter Fratzi, "Mineralized Collagen Fibrils: A Mechanical Model with a Staggered Arrangement of Mineral Particles".

Journal of Materials Science: 33 (1998) 1497-1509, U. Akiva, H.D. Wagner, and S. Weiner, "Modelling the Three-Dimensional Elastic Constants of Parallel-Fibred and Lamellar Bone".

* cited by examiner

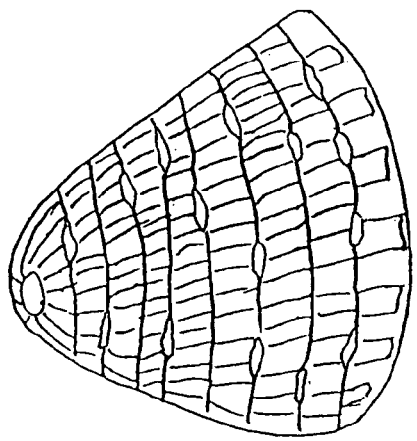
FIG. 5
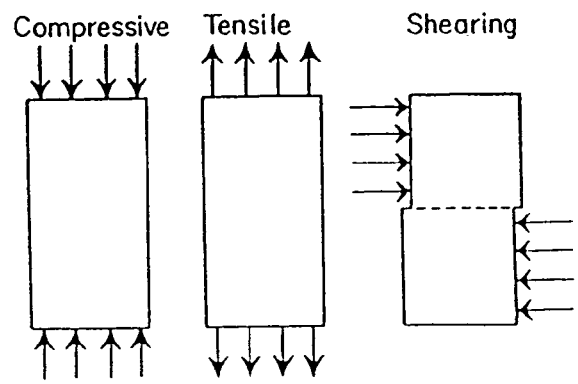
FIG. 6A
FIG. 6B
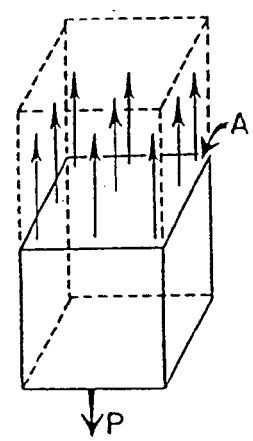
Stress = Force (P) / Area (A)
(S)
FIG. 6C
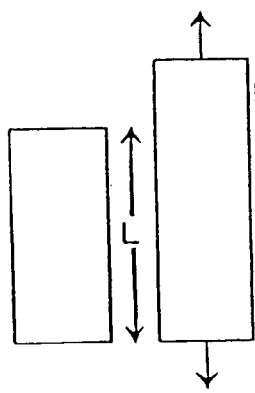
Strain = Deformation (D) / Length (L)
(e)

SYSTEM AND METHOD FOR MODELING BONE STRUCTURE

PRIORITY INFORMATION

This application claims priority under 35 U.S.C. § 119 from U.S. Provisional Patent Application Ser. No. 60/240,884, filed Oct. 17, 2000, and U.S. Provisional Patent Application Ser. No. 60/246,198, filed Nov. 6, 2000; each of which is hereby incorporated by reference in its entirety.

FIELD OF THE INVENTION

The present invention discloses a structural and mechanical model and modeling methods for human bone based on bone's hierarchical structure and on its hierarchical mechanical behavior. The model allows for the assessment of bone deformations and the computation of strains and stresses due to the specific forces acting on bone during function. The model further contemplates forces that do or do not cause viscous effects and forces that cause either elastic or plastic bone deformations characterized by fractures. In preferred embodiments the model is computerized, for example using computer simulation, imaging and rendering techniques.

BACKGROUND OF THE INVENTION

Material science defines the structural properties of an object as the properties that describe the object's makeup independent from its shape. Adult human bone has a complex structure and can be described as a four order hierarchy, arranged in decreasing size (Petersen, 1930). The first order, macrostructure (FIG. 1), comprises the structures corresponding to gross shape and differentiation between compact (or cortical) bone (FIG. 2) and spongy (cancellous or trabecular) bone (FIG. 3). Compact bone is present in the long bone shaft (or diaphysis). Spongy bone is present in the lower jaw (mandible), in the epiphysis of long bone shaft, and in flat and short bones. The second order (or microstructure) of compact bone includes lamellar systems (lamellae). Organized lamellae around vascular canals are referred to as osteons (harvesian systems) and disorganized lamellae among osteons are referred to as the interstitial bone. The second order also is comprised of related structures such as bone marrow (see e.g. Bloom and Fawcetts, 1986). The third order (or ultrastructure) of compact bone consists mainly of collagen bundles and hydroxyapatite crystallites; mucopolysaccharides amount to a small amout but may have a significant role. The fourth order of compact bone consists of molecular arrangements between organic and inorganic substances. For cancellous bone, the second order includes trabeculae, which comprise lamellar systems and related structures, e.g. bone marrow. The third and forth orders of cancellous bone are the same those described for compact bone.

The osteon comprises a haversian canal with concentrically arranged lamellae. Osteons of long bone are generally directed along the long bone axis. Osteonic lamellae are organized as consisting of an organic framework (mostly a collagen bundle) embedded in ground substances, such as proteins and water, and hydroxyapatite crystallites. The hydroxyapatite crystallites are oriented in directions analogous to those of the bundles. Osteons measure a few centimeters in length and are between 200 and 300 µm in diameter. The degree of osteon calcification (relative amount of hydroxyapatite crystallites) is variable from osteon to osteon as well as within osteons. These differences are proposed to be due to the process of bone renewal or remodeling. In this process, osteons are renewed continuously. Consequently, osteons at different degrees of calcification are always present in adult compact bone.

There is a spectrum of osteon types that refer to the arrangements of fiber bundle direction in the lamellae. Two osteon types, "longitudinal" and "alternate", are representative of the two ends of the spectrum. Longitudinal osteons consist of bundles with a marked longitudinal spiral course. Alternate osteons consist of bundles with a marked longitudinal, oblique, and transversal course in successive lamellae (Frasca et al., 1977; Giraud-Guille, 1988; Ascenzi A. et al., 2000). There are two types of lamellae, termed extinct (or longitudinal) and bright (or transverse or circularly-fibered) lamellae. Extinct (or dark) lamellae appear extinct (or dark) whereas bright lamellae appear bright under a polarizing microscope when the microscope and osteon axes are aligned.

Compact bone consists of about 40% minerals, 40% collagen, and 20% fluids. The major internal spaces or discontinuities of compact bone include the vascular system, pits and cavities (lacunae), narrow channels (canaliculae), fine porosity, and spaces between the mineral phases. The major internal material discontinuities of compact bone (FIG. 5), in order of decreasing size, are:

| | |
|---|---|
| Vascular system | 20–50 µm |
| Lacunae | 4–6 µm |
| Canaliculae | 0.5–2 µm |
| Fine porosity | 600–800 Å |
| Spaces between mineral phases | 50–100 Å |

Cancellous bone consists of trabeculae, i.e. osseous structures with either a sheet-like or a rod-like configuration. These structures interlace to form a lattice-like or spongy biological structure (FIG. 3). For example, both types of trabeculae are present in the calcaneous; however, up to 3% of the rod-like configurations are tubular due to the vascular canal running through them. Therefore, they are similar to the harvesian system. In general, tubular trabeculae appear to have a relatively simple structure. Collagen fibrils run mostly parallel to the long axis of tubular trabeculae in the trabeculae outer portion and perpendicular in the inner portion. Although the true density of fully calcified cancellous bone is a little lower and the proteoglycan content a little greater than those of the fully calcified compact bone, the substantial difference between compact and cancellous bone resides in the porosity. The cancellous bone porosity, which ranges from 30% to more than 90%, is mainly due to the wide vascular and bone marrow intrabecular spaces. As is seen in compact bone, levels of calcification vary from trabecula to trabecula and within trabeculae.

The connections and orientations of trabeculae are found to have precise patterns, which are believed to relate to specific mechanical properties. The structure of the cancellous bone in the head and in the neck of the femur is usually given as an example of the correlation between the orientation of the trabeculae and the linear distribution of the principal forces during load bearing (stress trajectoral theory (Bell, 1956)). In general, such correlation between the orientation of the trabeculae and the linear distribution of the principal forces during load bearing is still under study because while in line with the mathematical calculations, the possible effect of muscle traction is complex (Koch, 1917;

Rybicki et al., 1972). Nevertheless, there is a close relationship between the number and arrangement of trabeculae and the strength of cancellous bone (see e.g. Kleerekoper et al., 1985). This is evidenced by the age-induced loss of trabeculae (see e.g. Birkenhäger-Frenkel et al., 1988). Since this loss is rather selective (i.e. transverse trabeculae disappear more frequently than vertical ones in the central zone of the osteoporotic vertebral body; entire trabeculae totally disappear in elderly women and a sharp fall in trabecular number is observed in elderly men), it is possible that cancellous bone contains some bundles of trabeculae whose main function is to resist mechanical forces while others have mainly a metabolic role.

The mechanical behavior of an object, or the response of an object to forces, of an object depends on the structure of the object. If the object is comprised of a hierarchical structure, the mechanical behavior of the object varies from order to order. That is, each order or level of the hierarchy responds to forces according to the structures and relationships within that order. Overall mechanical behavior of the object is ultimately determined by the mechanical properties of the different orders. Therefore, the mechanical properties of an object will vary with the hierarchical structure of the object. Bone is an example of an object where the mechanical behavior and mechanical properties are dependent upon this kind of hierarchical structure.

Mechanical properties of bone have been and are being investigated at various hierarchical levels through invasive (sample isolation) and non-invasive testing. Osteonic trabecular lamellae, osteons, trabeculae, and macroscopic compact and cancellous bone samples have been and are the objects of such studies. Micromechanical results include Ascenzi A. and Bonucci, 1964, 1967; Ascenzi A. and Bonucci, 1968, 1972; Currey, 1969; Ascenzi A. et al., 1985, 1997, 1998; Hohling et al., 1990; Ascenzi A. et al., 1990, 1994; Marotti et al., 1994; Ziv et al., 1996; Ascenzi M.-G., 1999a, 1999b; Huja et al., 1999; Zysset et al., 1999; Ascenzi M.-G. et al., 2000. Macromechanical results include Hazama, 1956; Cook and Gordon, 1964; Carter and Hayes, 1976 and 1977; Carter et al., 1976 and 1981; Carter and Spengler, 1978; Hayes and Carter, 1979; Burr et al., 1988; Cater and Carter 1989; Jepsen and Davy, 1997.

Even though numerous publications have addressed bone micromechanics in recent years, many biomechanical issues relating to bone are still not understood due to the lack of reliable or predictive models. The lack of inclusion of such micromechanical properties in current models of bone functions and behavior have severely limited their usefulness in predicting macromechanical properties. These properties include the bone behavior in response to external forces or identifying the requirements of bone reconstruction and prosthesis. However, the inclusion of these factors requires the development of methods and studies that may provide reliable and reproducible results.

The present invention describes a method to understand and predict the behavior of bone. The method includes a model of macroscopic bone which is constructed in terms of bone's hierarchical structural and mechanical properties and their interaction with forces acting on the macroscopic bone, including forces associated with the ordinary functioning of the body and forces applied clinically. The method can be applied to any bone structures, including human bone and the bones of vertebrates in general. The model applies to normal bone, and to pathological bone, when the pathology either does not alter the structural hierarchy, or when the alterations are characterized. The model is also applicable to fossilized bone.

SUMMARY OF THE INVENTION

The present invention contemplates a model of macrostructural properties of bone. The model comprises hierarchical structural and hierarchical mechanical properties of microstructure of the bone and includes interactions of the bone with internal and external forces. In a preferred embodiment, the bone that is modeled is either compact bone or cancellous bone. In an additional preferred embodiment, the mechanical properties used in the model are selected from the group consisting of tension, compression, shear, bending, torsion, prestress, pinching, and cement line slippage.

The present invention also contemplates methods of predicting deformation and fractures of bone and for identifying the requirements of bone reconstruction and prosthesis using the model of the present invention.

BRIEF DESCRIPTION OF DRAWINGS

FIG. 5. Cross-section diagram of an osteon sample illustrating the arrangement of canaliculae and lacunae relative to lamellae.

FIGS. 6(a)–(c). (a) Types of pure forces. (b) Definition of stress on an area on which the force is constant. (c) Definition of unidirectional strain for D much smaller than L.

DETAILED DESCRIPTION OF THE INVENTION

Figure 1:
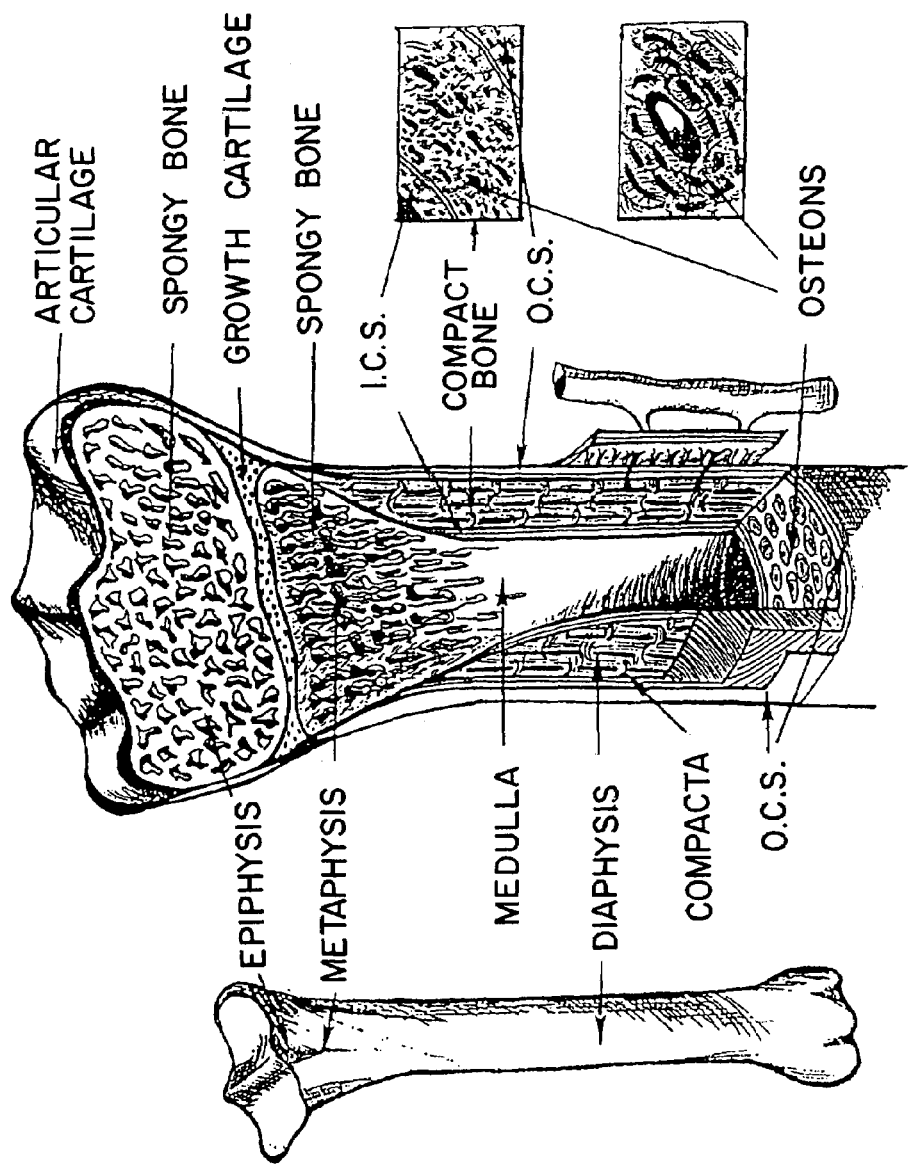
FIG. 1. A schematic representation of the upper third of the tibia; i.c.s. and o.c.s. stand for inner and outer circumferential systems, respectively. Both compact and cancellous bone are represented.
Figure 2A:
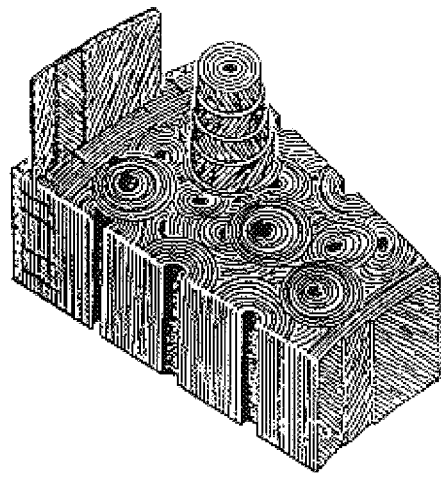
FIGS. 2(a) and (b). (a) Diagram of a diaphysis sector of cortical long bone. The osteons or haversian system (HA) are located between the outer OL and inner IL circumferential lamellae. The osteonic lamellae are disposed cylindrically around the haversian canal (HC). (b–d) Cross-sectioned osteons as seen (b) under a light microscope; (c) in a microradiograph; and (d) under the polarizing microscope.
Figure 2B:
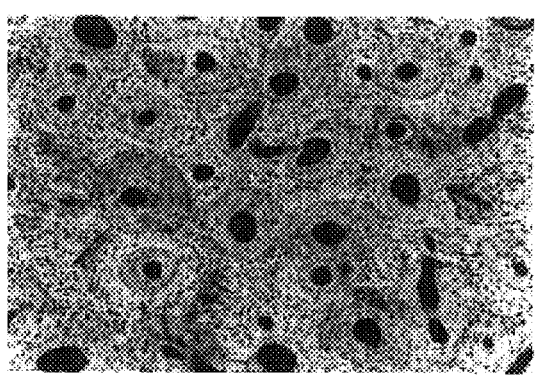
Figure 2C:
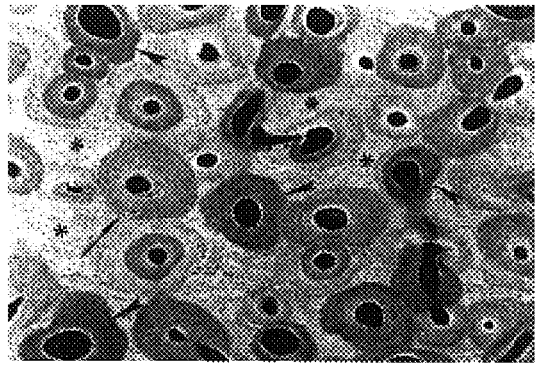
Figure 2D:
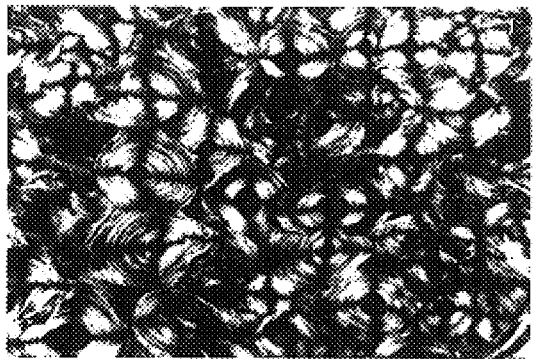

The present invention describes a method for modeling the anisotropic (direction-dependent) and non-homogeneous macrostructural properties of compact bone in terms of the microstructure. The model is based on the hierarchical structural and mechanical properties and bone interactions with internal and external forces. An example of such forces includes, but is not limited to, the ordinary functioning of the body. The model includes properties of the microstructure, in particular distributions of transverse lamellae of trabeculae and of alternate osteons, pinching of osteons, and slippage of osteons at the cement line.

Morphological and mechanical studies of bone show that at all hierarchical levels bone is anisotropic (the local mechanical properties are direction dependent), and non-homogeneous (the structure is not the same at different points). Nevertheless to simplify bone modeling, bone structure often is assumed to be homogeneous, isotropic (not direction dependent), transversely isotropic (one plane of symmetry), or orthotropic (three planes of symmetry). The simplifications of isotropy, orthotropy, and transverse isotropy give rise to unrealistic models because these simplifications that symmetries that do not exist. For instance, in such models stresses may be over- or under-estimated. When such models are applied to practical applications, for example bone implants, poor estimates of stress may give rise to screw loosening in implants. The simplification of homogeneity gives rise to unrealistic models because it disregards the hierarchy of the bone structure. The existing hierarchical models are based on homogeneity theory, finite element analysis, and classic and Cosserat elasticity theories (see e.g. Katz, and Meunier, 1987; Crolet et al., 1993; Pidaparti and Burr, 1992). These models do not include important properties of the microstructure, which are included in the present invention and are described below.

The present model provides for modeling each level of the hierarchical structure of bone in terms of the structural and mechanical properties of that level. The model further provides for determining the relationships among the various levels.

In compact bone:
(1) Collagen bundles, hydroxyapatite crystallites, and mucopolysaccarides are organized in two lamellar types, bright, which are prestressed, and extinct lamellae. Lamellae show porosity.
(2) Lamellae are organized in osteons. Osteons show pinching under tension-compression cyclic loading.
(3) Osteons samples are organized in osteon sample groups on bone sections. Osteon groups show cement line slippage during torsion.
(4) Osteon groups are organized to complete a bone section. The collagen bundle direction distributions are used to complete this organization.
(5) Transverse sections are organized to complete the macroscopic bone.

In cancellous bone:
(1) Collagen bundles, hydroxyapatite crystallites, and mucopolysaccarides are arranged in bright and extinct lamellae. Bright lamellae are prestressed. Lamellae show porosity.
(2) Lamellae fill in trabeculae. Trabeculae show porosity.
(3) Trabeculae are grouped in trabecular sample groups on bone sections.
(4) Trabecular groups are organized to complete a bone section. The prevalent collagen bundle directions are used to complete this organization.
(5) Sections are organized to complete the macroscopic cancellous bone.

To produce the model, each microstructural level of the hierarchical bone structure commences with the microstructural components and proceeds through the macrostructure. Each element of the assembly is correlated with mechanical properties either determined from literature sources or that are newly estimated. Homogenization methods are used to assemble the structure at one level with the structure at the next level, and so on, to build a hierarchical model. The finite element method allows for the computation of strains and stresses throughout the model.

The invention results in a model of macroscopic compact and cancellous bone that respects the hierarchical, structural, and mechanical properties starting from the microstructural components. The model may be applied to all bones to result in a model for each bone of the skeleton.

The present invention further defines methods of predicting deformation and fractures of bone and identifying the requirements of bone reconstruction and prosthesis using the model. From the specific forces that act on bone during function, the model allows for the assessment of bone deformation, strain, stresses, and fractures. Additionally, from the fractures and stress distribution, the model allows for the computation of strain deformation and forces that cause the observed fracture and stress distributions. The model also contemplates forces that do or do not cause viscous effects. The model contemplates forces that cause either elastic or plastic bone deformations as characterized by fractures.

The model includes torsional cyclic loading functions of two representative osteon types in terms of degrading properties such as stiffness and pinching, and increasing energy absorption. These mechanical property changes are correlated to the idealized or mathematical behavior of ultrastructural components, which includes yielding, buckling, and fracturing properties. The resulting algorithms and behaviors comprise an osteon model, which simulates fracture propagation in osteons under cyclic torsional loading in terms of microcracking, debonding, void growth, and fiber breakage. Verification of the model is demonstrated by checking that the model produces the fractures observed in osteon samples that are separately submitted to tension, compression, and shear.

The model also includes simulation of microstructural fracture propagation in bone. Because of the dependence of the macrostructure's mechanical properties on microstructure, the model will provide an improved understanding of properties of long bone, such as fracture propagation, including a better understanding of how human bone macrostructure responds to forces acting on it.

The model will have application in many areas, including without limitation:
the mechanics of natural composites and the manufacture of new composites, since bone is a natural composite material;
the identification of the fundamental requirements of bone reconstruction and prostheses (which will increase design effectiveness and reduce testing and related cost); and
the microstructure of vertebrates whose microstructure is similar to human's.

Definitions

The present invention spans through both elastic and plastic ranges. As used herein, the term "elastic range" refers to the stress and strain values for which the material structure does not break and returns to its original shape when the force is removed. As used herein, the term "plastic range" refers to the stress and strain values for which the material structure does break and therefore does not return to its original shape when the force is removed. When an increasing force (starting from zero) is applied to a material, the material undergoes first elastic and then plastic deformation. Any bone type can undergo elastic deformation only or both elastic and plastic deformation depending on the force magnitude. Elastic and plastic deformations provide a starting point to predict strain and stress distributions and fractures of bone. The model also may be used to compute the stress distribution from the strain distribution and strain distribution from elastic and plastic deformations. It further identifies the requirements of bone reconstruction and prostheses.

As used herein, the term "boundary conditions" refers to the relative movements of the boundaries of the various hierarchical structures under loading. In a specific embodiment, the behavior of the cement line under loading is the boundary conditions for the osteon and the interstitial bone between which the cement line lies.

The term "pinching" refers to a sharp change of stiffness of bone. As used herein, the change in stiffness can be either from increasing stiffness to decreasing stiffness or from decreasing stiffness to increasing stiffness. In a preferred embodiment, the change presents itself on each half-cycle.

The term "material analog" refers to a model or reproduction produced from material, as distinguished from a mathematical or computer model.

The term "distraction device" refers to an apparatus that generates bone by stimulating growth of existing bone by application of forces to such existing bone.

As used herein, the term "strain distribution" refers to a measure of the degree of elongation at any point on a sample. In a preferred embodiment, the sample is bone.

The term "stress" refers to the force per unit area.

The term "stress distribution" refers to strain distribution and on the mechanical property distribution throughout the body.

The term "corrected break area" refers to the actual bone area, except for the lacunae and canaliculi, subjected to stress in the vicinity of a break.

The terms "viscous effect" and "viscoelastic" refer to a system that exhibits behavior that combines liquid-like and solid-like characteristics.

Factors

Mechanical Properties

Various mechanical properties are included in the model of the present invention. The properties will be correlated with each hierarchical level of the bone to produce the model. A non-limiting list of such properties is disclosed and described herein.

The mechanical properties of bone are quantified by parameters or coefficients that describe the response of bone to tension, compression, shear, bending and torsion. Tension, compression, and shear are termed "pure forces" because each of them is recognized by the effect (the deformation) produced in the body to which it is applied (FIG. 6). A tension (tensile) force tends to lengthen the body to which it is applied, while a compression (compressive) force has a tendency to shorten the body. A shear force tends to make one part of a body slide in a direction opposite to that of an adjacent part. Bending and torsion (FIG. 7) are a combination of tension, compression and shear.

The effect of the application of one of the above-mentioned forces to a body at a natural state is described in terms of strain and stress. Strain is the measure of dimensional changes in a body and is computed by means of the deformation (Antman, 1995). Since in general the value of strain changes from point to point throughout the body, more properly one refers to strain as the strain distribution throughout the body, which provides the value of strain at each point of the body. The tendency of a body to be deformed by the application of a force is resisted by the internal force among the molecules composing the body. Such resistance is measured by the stress, which is a force per unit area. Similar to strain, in general the value of stress changes from point to point throughout the body. More properly one refers to stress as the stress distribution throughout the body, which provides the value of stress at each point of the body. The stress distribution depends on the strain distribution and on the mechanical property distribution throughout the body. What all elastic structures have in common is that the stress distribution is a linear function of strain within the elastic range (Hooke's Law; see e.g. Jones, 1975). Beyond the elastic range the relationship between stress and strain distributions depends on the particular structures. For instance, the mechanical testing of a specimen provides a stress-strain diagram, which allows the study of the relationship between stress and strain.

Studies indicate that the mechanical behavior of longitudinal and alternate osteon samples at equal degree of calcification, as assessed by the method of Amprino and Engström (1952), differs because of their structural difference. The comparison of experimental stress-strain diagrams for longitudinal and alternate osteons shows that under monotonic tension and torsion, longitudinal osteon samples resist stresses better than alternate osteons; while under compression, shearing and bending, alternate osteon samples resist stresses better than longitudinal osteons. Under cyclic tension-compression loading, longitudinal osteon samples show a larger energy loss and lesser pinching degradation per cycle than alternate osteons; longitudinal osteon samples show a greater strain increase during compression than tension. The opposite is true for alternate osteons.

Figure 8A:
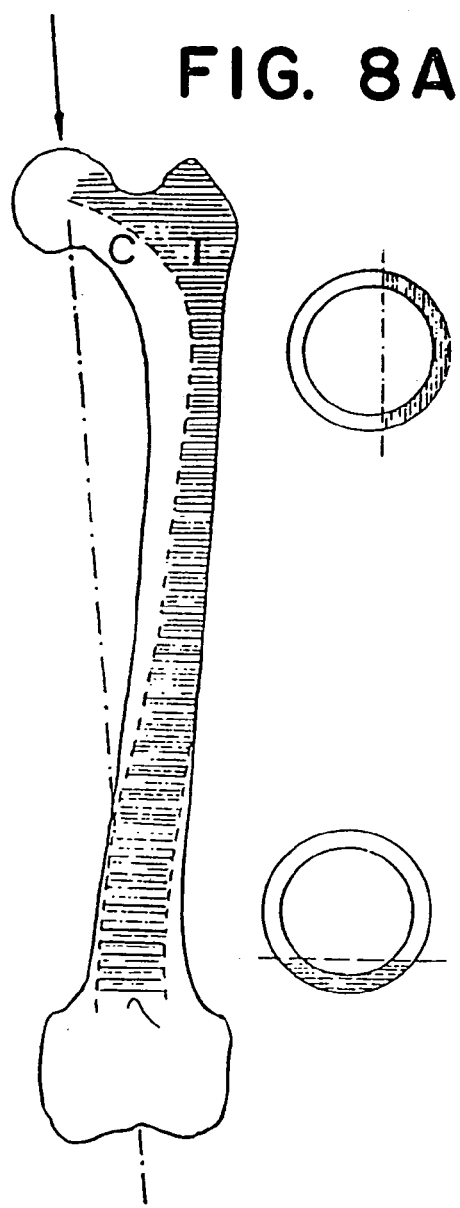
FIGS. 8(a) to (d). (a) Bending of femur due to gravity. C indicates the area under compression and T indicates the area under tension. Diagrams (b), (c), and (d) display the distribution of transverse and longitudinal lamellae in the sections prepared from the upper, middle and lower shaft, respectively. The posterior, anterior, medial and lateral regions correspond to the top, bottom, left and right regions, respectively, on the page. The distdnce between the centers of two adjacent square symbols measures 1.86 mm. The size of the square symbol is proportional to the ratio of the bright area in circularly polarized light to bright area in a dark field illumination. The regions with dominant transverse lamellae correspond to the regions with concentration of larger squares in the upper medial, middle medial-posterior and lower posterior shaft, which correspond to the areas of compression in (a). The regions with dominant longitudinal lamellae correspond to the regions with concentration of smaller squares in the upper lateral, middle lateral-anterior, and lower anterior shaft, which correspond to the areas of tension in (a).
Figure 8B:
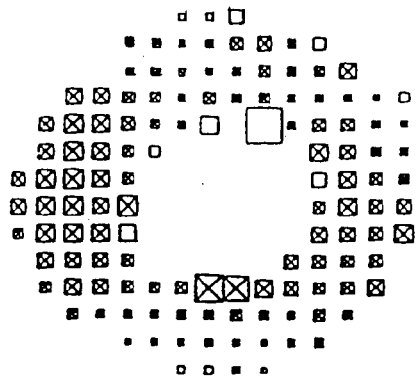
Figure 8C:
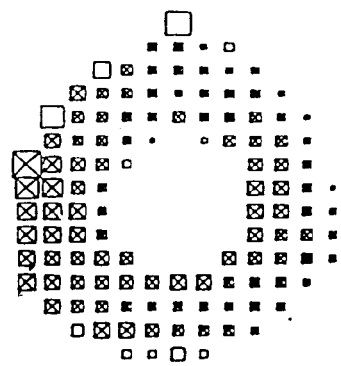
Figure 8D:
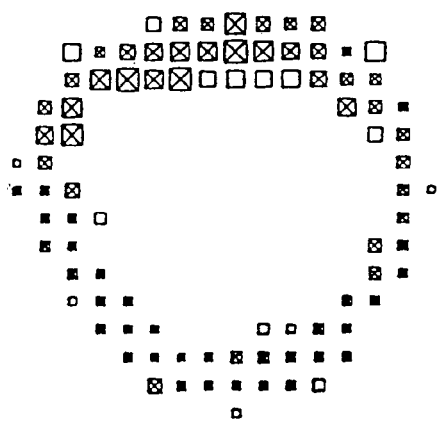

The macroscopic mechanical properties have been found to depend on and to be explained by the microstructure. In particular, they have been found to depend on the numerical presence of osteons, the size and percentage volume of osteons, and collagen fiber orientation (Currey, 1959; Evans and Vincentelli, 1969). As early as 1873, Rauber considered the correspondence between bone micro- and macro-structure. He hypothesized that the structure of osteons and interstitial bone in the long bone shaft relates both to their distribution in the shaft under normal conditions, and also under pathological conditions that do not alter the bone's hierarchical configuration. This hypothesis was later confirmed (Portigliatti-Barbos, 1983, 1984, and 1987; Boyde et al., 1984; Ascenzi A. et al., 1987a and 1987b; Ascenzi A., 1988; Carando et al., 1989 and 1991). Specifically, the distribution of dark lamellae (whose bundles have a transverse and oblique course) and of bright lamellae (whose bundles have a longitudinal course) in osteonic and interstitial bone follows a characteristic non-random pattern. Studies indicate that this distribution is consistent with the distribution of bending forces usually operative on this bone (Ascenzi M.-G., 1999a). For example, the femoral dominant distribution of dark and bright lamellae displays a clockwise rotation of approximately 90° in sequential sections from upper, middle, and lower third of the shaft (Portigliatti-Barbos, 1983, 1984). In fact, because of the femoral overall shape which includes two curvatures (an anterior-posterior curvature and a lateral-medial curvature), gravity on the body results in the bending of the femur. Because bending always includes an area of tension and an area in compression, the femur presents an area in tension and an area in compression (FIG. 8a). It turns out that the femoral dominant distribution of dark (bright, respectively) lamellae coincides with the area in tension (compression, respectively) (FIG. 8b). Recent work also has found that the above-mentioned transverse/longitudinal lamellar distribution is consistent with the distribution of alternate osteons (Hert et al., 1994). Neither the transverse/longitudinal lamellar distribution nor the alternate osteon distribution have been included in prior models of bone structure. Transverse/longitudinal lamellar distribution and the alternate osteon distribution are included in exemplary models of the present invention.

Additional Factors

The following provides a non-limiting list of factors that may be included in the models of the present invention, and which are used in exemplary embodiments.

(1) Fracture of macroscopic bone. The invention incorporates fracture dynamics into the bone model and modeling methods, including mechanisms by which a fracture starts and spreads. Unlike other models of bone, fracture propagation is modeled in terms of ultrastructural components. The literature indicates that the fracture mechanism of bone depends on bone structural and composition properties such as collagen architecture and collagen content (e.g., Jepsen et al., 1999). In 1969, Evans and Vincentelli showed significant differences among osteons of various bones (fibula, tibia, and femur) in the "corrected break area", which is the actual bone area, except for the lacunae and canaliculi, subjected to stress in the vicinity of a break. Characteristic differences were found between the means of the corrected break area for groups of longitudinal and transverse (i.e., consisting of transverse lamellae) osteons and of osteon fragments of the femoral and tibia sections and for groups of the transverse osteons and fragments of the tibia and fibula sections. The percentage of the "corrected break area" of transverse osteons and their fragments in the tibia and fibula sections was also statistically different. Another study (Vincentelli and Evans, 1971) established a relationship among macromechanical properties, collagen bundles, and calcification in the shaft of long bones. Furthermore, fracture lines appear to follow the cement lines between osteons and lamellar boundaries within osteons (Simkin and Robin, 1974) where the bone is weaker. According to the invention, inclusion of the differences between the means of the corrected break area for groups of osteons would increase the predictability of the present model compared to prior art models.

(2) The prestress distribution in bone. The models and methods of the invention incorporate computations of the stress distribution in long bone so as to include pre-stress (Currey 1964; Ascenzi A. and Benvenuti, 1980). Stress distribution in long bone depends on structural and composition properties such as collagen architecture and collagen content. Bone areas where collagen bundles are transverse and oblique to the long bone axis are prestressed. Such prestress, estimated on the order of 0.1 GPa, is too large to be disregarded. It locally impacts the stress produced by forces acting on bone (see Ascenzi M.-G., 1999a). Newly estimated prestress variables are included in the present invention (Ascenzi M.-G., 1998a and 1999b). The newly estimated prestress was evaluated through the structural and mechanical modeling of isolated lamellar samples, and has been shown to be a realistic approach. See e.g., A. Meunier, 1999. Inclusion of this prestress into the model of the present invention allows one to more accurately model bone in terms of computation of stresses.

(3) The phenomenon of "pinching". The invention for the first time incorporates pinching into bone models and modeling methods. Pinching is the mechanism of yielding and buckling of collagen bundles under loading beyond the elastic phase. It is an important step in the formation and propagation of fractures. The understanding of pinching requires detailed analysis of osteon mechanical behavior. In fact, while the stress-strain curves for monotonic loading under tension, compression, and torsion show trends no different from those recorded from macroscopic bone samples, the tension-compression hysteretic loops showed a new behavior for osteon samples not observed in macroscopic samples (Ascenzi et al, 1985 and 1997). The new behavior observed is that tension-compression hysteretic loops of osteons demonstrate S-shaped half-cycles. This phenomenon has been observed and studied only relative to earthquake-resisting structures. In such context the behavior is usually called "pinching" (see, e.g. Narayanan and Roberts, 1991). Pinched hysteretic loops are typical of structures that incorporate a matrix that cracks and reinforcements that yield or whose members buckle when subjected to compressive loads. In osteons, the shape and dimensions of hydroxyapatite crystallites and the relationship of these parameters to the organic components of the matrix are only partially known. Not all collagen bundles are completely calcified. Those that are not calcified take up crystallites only on 400 Å bands (Ascenzi A. et al., 1965). Hence such bundles may be comprised of relatively more stiff 400 Å bands separated by relatively more flexible non-calcified collagen segments.

Pinching in osteons is hypothesized to be mainly localized at the partially calcified bundles. Therefore, in osteons, either bundles yield in tension and buckle in compression while crystallites fracture and detach from collagen, or crystallites fracture and detach from collagen in tension while collagen yields in compression. Thus, cyclic tension-compression loading shows pinching. Since cyclic torsional loading involves tension and compression, cyclic torsional loading is expected to show pinching. Nevertheless, it may be that the disruption created by torsional loading is too disordered, in comparison to that due to tension-compression, to allow closing of lesions and resolution of members as controlled as under tension-compression. In any event, if cyclic torsional loading of osteons shows pinching, pinching is included in the invention applied to macroscopic compact bone torsional loading.

(4) Macrostructure and mechanical loading studies of whole bone or macrosamples. The invention takes account the influence of bone microstructure in evaluating mechanical loading of whole bone and of bone macrosamples. In the literature, for example the torsional loading in bone has been analyzed using finite element analyses (see e.g. Hazama, 1956; Pfafrod et al., 1972 and 1975; Knets et al., 1973; Miller and Piotrowski, 1974; Evans, 1978; Martens et al., 1980; Moreland, 1980). However, models presently do not completely reflect the changing properties of bone at the microstructural level. Similarly, cancellous bone has been described as continuous and isotropic, which does not reflect the high porosity and the changing details (such as collagen bundles direction and lamellar structure) at the microstructural level. The elastic and plastic moduli change locally in relation to the microstructural properties.

Such studies ignore most of the mechanical properties of the microstructure (because macroscopic samples do not always have the same mechanical properties as the microstructure that comprises them) and therefore do not provide a realistic understanding of bone mechanics. For instance, pinching is present in longitudinal and alternate osteons but not in macroscopic compact bone samples during tension-compression cyclic loading; also the torsional stiffness varies from osteon samples to osteon groups and relative to that of larger compact bone samples (Lakes, 1995). Lakes shows that the torsional shear moduli of osteons are much larger than shear moduli obtained for macroscopic samples. That is, slender specimens are stiffer than thick ones; the lower stiffness in thick specimens is attributed to slippage of osteons at the cement lines during torsion of macrosamples. Such slippage is described well by Cosserat elasticity theory since it allows a moment per unit area in addition to the usual force per unit area of classic elasticity theory. The inclusion of this factor into the model impacts, for example, the simulation of fracture propagation. The fracture propagation model is able to simulate the slippage of osteons at the cement lines during torsion and therefore the experimentally obtained results regarding fractures spreading along the cement line.

Local Properties and Bone Modeling

The knowledge of the mechanical properties and of the strain and stress distributions of compact and cancellous bone under specific loading is necessary in all contexts where the local behavior of bone is in question. For example, stability is the crucial characteristic of an osteotomy fixation device. When a tibia requires an osteotomy, the device that holds in place the two bone edges created by the cut (osteotomy) can only allow for micro-movements of one edge with respect to the other during function, such as walking, to be successful. The stability of device depends on its shape, and material, and on the number, position and inclination of the pins that secure the device to the tibia. The best position and inclination of pins for the stability of the device depends on the spot chosen, that is on the local property of the tibia. The anisotropy and non-homogeneity of the tibia make a difference with respect to the screw loosening while walking. In fact, the screw may or may not get loose if the chosen spot is more or less resistant to the force that it takes for the pin to get into place, if one inclination is chosen instead of another one, if the spot is prestressed in one direction or another. The question of osteotomy fixation stability cannot be fully studied with a computer bone model that does not take into account the hierarchical structure of bone that renders bone anisotropic and non-homogeneous. Because if the model assumes less than that, the local information is lost and the bone shows the same properties where it should not.

Another example refers to cemented implants. The local bone conditions affect the bone-implant interface. The loosening rates in cemented implants, especially in younger, active persons, is partially due to the local bone mechanical properties. This problem has led many investigators to pursue methods of cementless fixation. In the meantime a great deal of attention is being focused on the bone-implant interface and the factors affecting its strength. A thorough solution to the problems involves the knowledge of the local bone mechanics.

Simulation of Fracture Propagation

The fracture propagation model of either compact or cancellous bone under specific loading follows the same steps as the fracture propagation model of single osteon samples under torsion (See, Example 2, Part E, Steps 1–19). The computer program may be based on any suitable simulation program, for example, a Monte Carlo simulation. The fracture propagation steps are applied to the finite element mesh for the compact or cancellous bone in question, instead of to the finite element mesh of single osteon samples.

The purpose of the fracture model is to show that cumulative micro-cracking, de-bonding, void growth and fiber breakage associated with repeated loading of osteons causes a progressive loss of stiffness and pinching, and increase of energy absorption.

The fracture model reflects the following hystological/physiological observations. Fluids occupy vascular canals, canaliculae and lacunae, which are interconnected. The flow of liquids under stress can absorb large amounts of energy, increasing the toughness of bone. Large strains may be accommodated by the organic phase (e.g. collagen, mucopolysaccharides). When a strain is sufficient to cause cracking, the organic phase may also contribute to the dissipation of energy at the front of a propagating crack. Crack propagation also appears to be arrested in the presence of canaliculae and lacunae. In fact, when the crack gets to a hollow space, it just stops because at the hollow space there is no more resistance, no more material to rip. Therefore, discontinuities to some extent increase the robustness of bone rather than increase its tendency for brittle fracture (Currey, 1962). In the case where a crack enters a discontinuity, the front tends to be blunted, hence reducing the stress concentration factor (i.e. the level of stress necessary to create a crack) and slowing crack propagation. When a crack is forced to enter a vascular canal, the radius at the tip of the crack becomes larger. Lacunae are probably more likely to act as stress concentrators than canaliculae because of their generally ellipsoidal cross-section and because they are generally oriented normal to the long axis. Stress concentrators are define as entities that raise the stress concentration factor. However, their much smaller size precludes them from acting as fracture initiators (i.e. causes for the structure to begin fracturing) until or unless plastic deformation has created cracks at the tip. Fractures spread along cement lines and lamellar interfaces.

Additional Applications

The model also can be used with complimentary applications and technologies. An example includes, but is not limited, to combination with software to model soft tissue (such as the one developed by the company Infocus, Sylicon Valley, Calif.). Material analogs of bone can be obtained by means of 3D printers (see e.g., the printers manufactured by Stratasys-3D printing in Eden Prairie, Minn.). Implants and distraction devices will be manufactured by computer guided robots. See, e.g., Mah and Hatcher, 2000. The present model will provide the model of the bone structure to be distracted and during distraction.

The application of modeling to imaging (e.g., clinical MRI and CAT scan x-ray imaging) of human bone offers the prospect of a qualitative leap in the predictability, effectiveness, and convenience of surgical, orthodontic, orthopedic and other medical interventions. Embodiments of the model can enable medical professionals, based on patient specific data, to visualize how bone in various parts of the body will grow and heal in response to medical interventions. First, the current lack of bone local mechanical properties impairs the comparison between natural and synthetic bones. Second, the current lack of knowledge of mechanical properties, strain and stress distributions throughout the bone, impairs the research for new synthetic bones to move towards the same properties. For instance, the latest synthetic long bone is made out of fiber-reinforced glass (Szivek, 2000) of unknown local mechanical properties. There are no reports of synthetic porous structures with the interconnecting pores having the same stiffness and strength characteristic of human trabecular bone. Even the most popular synthetic closed-cell polyurethane foams (such as Daro, Butler, Wis.) which have a structure that shows similarities with human trabecular bone are homogeneous in theory and with inhomogeneities difficult to control in practice. In any event the non-homogeneous hierarchical structure of human bone is not even close to being imitated. Third, the current lack of knowledge of mechanical properties and of strain and stress distributions throughout the bone, impairs bone reconstruction, bone grafting, placement of screws, insertion of prostheses.

The invention is applicable to the bones of other vertebrates whose bone structure somewhat differs from that of humans. For instance, the invention would give valuable results on the prevention and healing of fracture in equine bone. Currently, the micromechanical bone studies of vertebrates are scarce, often limited to a few small animals, such as mouse, dog, and sheep. Because of that, the results on human bone microstructure are erroneously used in studies of vertebrates to which they do not apply (Riggs et al., 1993a, 1993b).

The present invention provides a more realistic prediction of the macroscopic bone mechanical properties, strain, and stress distribution than computer models based on omission of either anisotropy or non-homogeneity of bone. Moreover, this invention provides more realistic prediction than purely mathematical models, that is models based on hypotheses, which are not based on experimentation. The literature is full of research on bone microstructure, which employs purely mathematical models of osteon behavior (Pidaparti and Burr, 1992). Such approach is limited, often unrealistic and does not always predict biological phenomena. The invention is flexible so as to include new experimental findings of bone structural and mechanical properties. This ensures the invention's realistic characteristic insertion of prostheses, etc.

EXAMPLES

The present invention will be better understood by reference to the following Examples, which are provided by way of exemplification and not by way of limitation.

Example 1

To produce a model of the present invention, compact bone is subjected to any method that may produce non-invasive slices of biological structures that are known in the art (i.e., μCT-scan or micro computerized tomography). Images then are stored in a computer and a 3-dimensional-reconstruction is applied using a standard method known in the art (see e.g. Materialise, XYZ Scientific Applications, Inc. Livermore, Calif.). The high resolution of a μCT-scan (about 30 μm) allows for determination of the outline of osteons, of osteons' vascular canals and interstitial bone. Also the 3D-reconstruction shows varying shades of gray, which represent the degree of calcification. Osteons are filled with structure by means of the two lamellar types (bright and extinct lamellae), which have been previously assembled. The criteria by which the lamellar structure is drawn into each osteon follows the distribution of alternate osteons (Hert, et al. 1994) and the distribution of dominant collagen fibril directions (Portigliatti-Barbos, 1983, 1984, and 1987; Boyde et al., 1984; Ascenzi A. et al., 1987a and 1987b; Ascenzi A., 1988; Carando et al., 1989 and 1991).

Figure 9A:
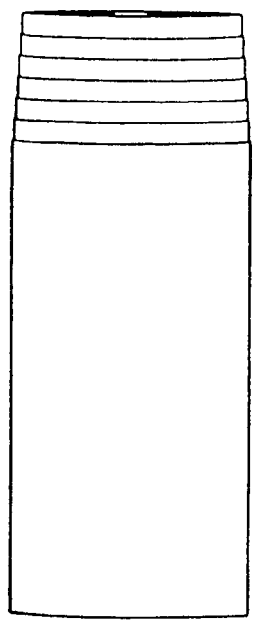
FIGS. 9(a)–(c). (a) The osteonic lamellar model is a laminate, which consists of fiber-reinforced unidirectional laminae. (b) The interstitial lamellar model is a portion of the osteonic lamellar model. The figure shows three thin laminae (lamellae) and a thick lamina (portion of cement line). (c) On a small laminar element of constant thickness, the principal material axes are labeled 1, 2, and 3. Direction 1 is parallel and direction 2 is perpendicular to the fibers. Direction 3 is the radial direction perpendicular to the page. Circumferential and axial directions are labeled $\Theta$ and z. The angle between the circumferential direction and direction 1 is called $\gamma$.
Figure 9B:
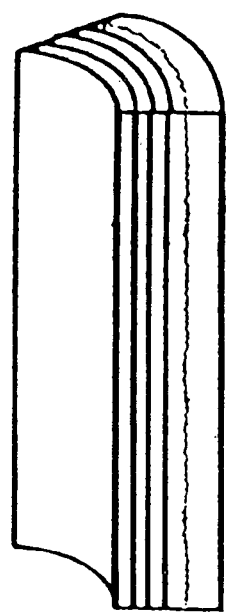
Figure 9C:
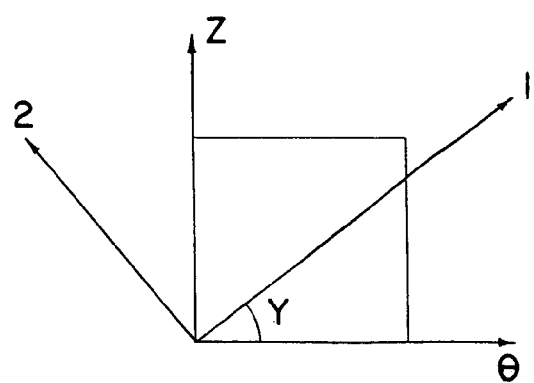

The structure of the osteonic lamellar model consists of a laminate whose length, width and height correspond to a cylindrical shell circumference, thickness, and height (FIG. 9a). The structure of the lamella within the interstitial bone is modeled as a portion of the osteonic lamellar model (FIG. 9b). The layers are unidirectional fiber-reinforced laminae (FIG. 9c) of the same matrix and fibers. The matrix and fibers, i.e. individual components of the hierarchical structure, and not the microstructure as a whole, are each treated as homogeneous and isotropic.

All fibers, of which there are two types, are assumed to be circular in cross-section, randomly distributed in the transverse plane. The fibers of the first type have a diameter of about 800 Å and fibers of the second type have a diameter of about 200 Å. The fibers of the first type are proposed to be perfectly embedded in matrix (they are idealized to have essentially no gaps between them and do not move relative to each other). The fibers of the second type are proposed to be perfectly embedded in matrix only when bone undergoes physiological static loading. When bone undergoes physiological dynamic loading the fibers of the second type are given the option to move with respect to matrix in which they are embedded. Such displacement is specified following experimentation, such as boundary condition or de-bonding experiments. The experimentation may also dictate further conditions for the relative position of the two fiber types. Examples of such experiments are discussed below.

In the present model, the lamina with fiber inclination $\gamma$ is named $\gamma$-lamina. The thickness of the dark lamella ranges between 7 and 12 $\mu$m (Ascenzi A. et al., 2000). It is described by the sequence [82, −82] (Frasca et al., 1977). The notation [82, −82] refers to two $\gamma$-laminae where $\gamma$=82, −82. The thickness of the bright lamella ranges between 4 and 7 $\mu$m (Ascenzi A., et al., 2000). It is described by the sequence [−61.5, −41, −20.5, 0, 20.5, 41, 61.5] (Ascenzi M.-G., 1999b).

For the matrix, Young's modulus of 114 GPa, Poisson's ratio of 0.27, and ultimate strength of 0.59 GPa are assumed for hydroxyapatite (Katz and Ukraincik, 1971). For the fibers of the first type, Young's modulus of 1.2 GPa, Poisson's ratio of 0.35, yield strength of 0.002 GPa are used for collagen (Currey, 1969). For the fibers of the second type, Young's modulus of 1.1 GPa, Poisson's ratio of 0.23, are used for mucopolisaccarydes (Bourne, 1971). Depending on the degree of calcification, the matrix occupies up to 40% of the lamina volume without voids (Bonfield and Li, 1967). The cement line is modeled as homogeneous and isotropic: the Young's modulus of 70 GPa and Poisson's ratio of 0.27 (Philipson, 1965; Schaffler et al., 1987).

Since osteons vary with respect to the distribution of dark and bright lamellae, the model of an osteon with a specific distribution of dark and bright lamellae is obtained by assembling the model of dark and bright lamellae so as to follow the osteon's particular distribution. For instance, a model of the longitudinal osteon, which consists of dark lamellae, is made of 12 laminae. The fiber inclination angle changes from 82° and −82° six consecutive times. A model of the alternate osteon, which consists of alternating dark and bright lamellae, is made of 36 laminae. The fiber inclination angle increases by 20.5° from −82° to 82° and then decreases by 20.5° from 82° and −82° four consecutive times.

Information included for the present model may not be currently available for all bones that are evaluated. Any information that is needed for the practice of this invention may be obtained by experimentation using methods that are standard in the art. Additionally, methods that may be used to evaluate bone in one species may be used to evaluate a similar bone structure in another species. For example, the distribution of dominant collagen bundle directions is available for the shaft of the human long bone but not for other vertebrates nor for the mandible. For any compact bone the distribution of dominant collagen fibril directions can be obtained by applying the method of Boyde et al. (1984).

For cancellous bone the same method can be applied after embedding (soaking and letting dry) the bone in a conventional resin used for the specimens examined under the electron microscope. Such resin should not change the microscopic characteristics (birefringence) of the specimens, so that the image of the collagen bundle and hydroxyapatite needle directions under the polarizing microscope is not altered by artifiacts. An example of such a resin includes, but is not limited to, epoxy. Note that application of the invention to cancellous bone will model lamellae that form trabeculae, as compared with the osteons of compact bone, however trabeculae and osteons can both be modeled in terms of lamellae.

From the above-mentioned mechanical properties of matrix and fibers (e.g., Young's modulus and Poisson's ratio) the same types of mechanical properties for lamellae under various load types (such as tension, compression, shear, and torsion) will be deduced by means of standard fiber-reinforced laminate methods known in the art (see e.g., Jones, 1975; Vinson, 1993; Antman, 1995).

Based on mechanical properties of the lamellae, homogenization theory will allow for the deduction of the osteon, osteon group, and interstitial bone mechanical properties for compact bone and trabecular mechanical properties for cancellous bone. The mathematically computed mechanical properties of lamellae, osteons, osteon groups, interstitial bone, and trabeculae are compared to the experimental results. If the experimental results are not available for the particular bone to which the invention needs to be applied, the properties may be determined using the methods for mechanical testing as described herein. The mechanical properties of lamellae, osteons, osteon groups, interstitial bone, and trabeculae are used as input for the homogenization methods to deduce the mechanical properties of the desired macroscopic bone.

Results are included of a finite element model, which allows for the assessment of the mechanical properties of the sample. The sample dimensions before and after testing allow for the formulation of an equation that describes the deformation from the shape before testing to the shape after testing. The deformation equation allows for the computation of the strain distribution throughout the sample. For example equations see Antman, 1995. The combination of such strain distribution with the experimental diagrams, the known sample structure before testing, and the fracture patterns after testing allow for the computation of the elastic properties through standard finite element methods. Statistical student t-test (Moore and McCabe, 1989) is run across the sample's results to allow for comparison of mechanical properties across the samples and to allow statistical conclusions.

These studies provide the mechanical properties of all the hierarchical orders. Therefore, the mechanical property distribution throughout the bone in terms of the microstructural components is known. The finite element method is applied (see e.g. the software package Abaqus) to compute the bone response to any given force acting on it. Boundary conditions are entered as assumptions into the finite element method. The first step is to create a 3-dimensional mesh (see e.g. Couteau et al., 2000).

The bone overall shape is filled with "elements". These elements are used to represent the osteons present in the bone. For example, a hollow cylindrical portion of an osteon with an inner and diameter of 40 $\mu$m, an outer diameter of 220 μm, and height of 500 μm, is filled with about 600,000 elements. Mechanical properties and boundary conditions are the method's input. Boundary conditions express the movements of the boundaries of the various hierarchical structures under loading. For example, dynamic loading evidences bone's viscous behavior. The literature points to mucopolysaccharides or perhaps collagen as the microstructural component responsible for the viscosity. In the structural part of the invention the second type of fibers models the mucopolysaccharides. The fibers of the second type are free to move. Such movement at the interface between the fibers of the second type and the matrix is expressed by a boundary condition (to be determined experimentally). Another example, the behavior of the cement line under loading is the boundary conditions for the osteon and the interstitial bone between which it lies. If the boundary conditions of a specific bone, to which one wants to apply the invention, are not available in the literature; they can be assessed experimentally by applying methods described herein or that are well known in the art. The software application gives as output the strain and stress distributions throughout the bone.

The mechanical properties of compact bone microstructure (lamellae, single osteons, osteon groups, single trabeculae) can all be experimentally found with the following method (other acceptable methods, including non-invasive methods are available in the literature). Human cadaveric bone aged between 20–50 is obtained according to the US regulations. The cadaveric bones are chosen either free of pathology to apply the invention to normal bone or with a specific pathology to apply the invention to a specific pathology. The bone marrow is removed by standard anatomical techniques (Wickramasinghe, 1975). At least 15 samples of any of such structures (lamellae, single osteons, osteon groups, single trabeculae) are isolated from the surrounding bone. The samples have about the same size and shape. The shape is a parallelepiped, a cylinder, or a hollow cylinder (depending on the chosen structure) with lugs (see e.g. FIG. 4c) for mechanical testing. Sample preparation and selection of compact bone microstructure is achieved by the methods of Ascenzi A. et al. (1994, 2000). For example, although any technique can be used, the method of Ascenzi A. et al. (1994) is preferably used to isolate osteons. The preferred form chosen for isolation of osteon samples is a cylindrical shape around the vascular canal. In general, the shape and location of a structural sample are chosen in such a way so that all the properties of the structure are preserved. Mechanical testing of osteon samples (Ascenzi M.-G. et al., 2000) may include, but is not limited to, monotonic and cyclic testing in tension, compression, shear, bending and torsion. The methods conducted as described in Ascenzi A. and Bonucci, 1967; Ascenzi A. and Bonucci, 1968, 1972; Ascenzi A. et al., 1990, 1994; Ascenzi A. et al., 1985, 1997, 1998 have proven themselves successful. The testing is conducted within the elastic range and beyond the elastic range to study fractures. Sample preparation and selection of cancellous bone (single trabecula and trabecular groups) is achieved by any of the methods whose bibliography is listed in Mente, 2000. Each sample is measured (the three dimensions for the parallelepiped; base radius and height for the cylinder base inner and outer radii and height for the hollow cylinder) before and after isolation and before mechanical test. Change in dimensions before and after isolation and before mechanical test shows existence of prestress. The structure of the sample is assessed before or after the mechanical testing (Ascenzi M.-G. et al., 2000). The samples are tested mechanically under physiological conditions, that is wet at 21° C. Since both compact and cancellous bone are viscoelastic, the results of mechanical testing are time-dependent (Sasaki, 2000). Consequently the strain rate and testing frequency need to be prechosen and the computer modeling depends on such choices. The stress-strain experimental curves (either monotonic or cyclic) through the elastic and plastic ranges are evaluated and recorded. After the mechanical test, the bone samples are measured and observed under the optical microscope for fracture patterns.

Figure 13:
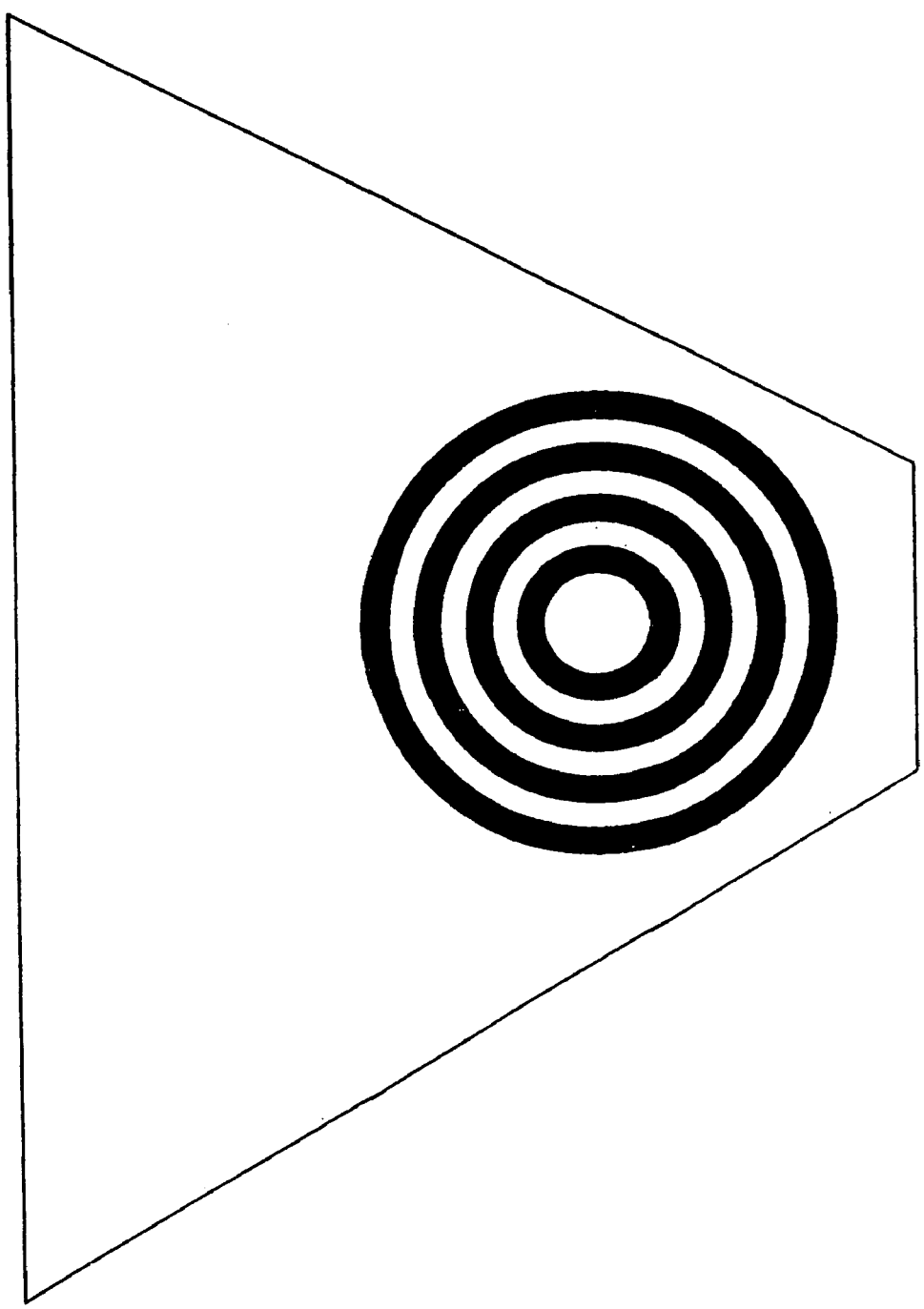
FIG. 13. A diagram that shows that around each osteon sample, a trapezoid was cut with a blade under a stereo microscope.

A trapezoid is cut around each osteon sample (see FIG. 13). For osteon immobilization during lamellar isolation, a portion of the bone material inside the trapezoid around the osteon is glued with Kemi®Cyak adhesive to a slide. The bright and the extinct lamella at the periphery of each osteon are dissected with a razor-sharp microscopic blade, obtained by filing a steel needle. To avoid fracture formation during straightening of each lamellar sample, such operation is performed gently on wet samples while checking under an optical microscope. The selection of external lamellae, of lesser curvature than internal lamellae, decreases the risk of fracture formation during flattening. The ends of each flattened sample are secured to two supports. The samples are measured as previously described and examined under an optical microscope to assess defects.

The mechanical loading on lamella on wet samples is conducted statically at 21° C. to complete rupture, with current model of the microwave extensimeter. Flattened bright lamellar sample is expected to resist tension along its length better than extinct lamellar sample. Indeed, the bright lamella is hypothesized to contain collagen bundles transverse to the longitudinal lamellar axis when enclosed in bone. Therefore, the enclosed lamella's transverse bundles strengthen the flattened lamellar sample in the direction of its length. The extinct lamella is hypothesized to contain collagen bundles parallel to the longitudinal lamellar axis when enclosed in bone. Hence, the enclosed lamella's longitudinal bundles after flattening are a source of sample weakness in the direction of its length because they are transverse to the loading direction. Fracture patterns of ruptured samples are studied under an optical microscope. Observation of fractures in ruptured samples will allow formulation of hypotheses on fracture nucleation and growth.

Since the interest is to test the isolated and flatten lamellar samples mechanically, the stresses present in the flatten lamellar samples before testing are assessed. To compute the stresses in the wet flattened lamellar samples, a computerized geometric-material model of a bright wet lamellar sample and of an extinct wet lamellar sample will be constructed, separately before and after isolation and flattening. The bright lamella includes prestress. It is hypothesized that the the stresses in the flat bright lamella are larger than the ones in the extinct lamella. Additionally, by taking into account that the periosteous is prestressed in tension, it may very well be that the outer circumferential system is prestressed in tension, too.

The geometry of the model is based on (1) dimensions (inner and outer radii, height, and dimension variations) of wet lamellar samples before isolation from surrounding alternate osteon and after isolation and flattening (width and length, and dimension variations) and (2) structure of lamellar sample. Therefore, dimensional measurements are needed. The structure model also is based on the lamellar structural components' arrangement. Therefore, lamellar structure under a confocal microscope will be assessed.

Example 2

A. Sample Preparation, Measurements, and Experimentation

Figure 4A:
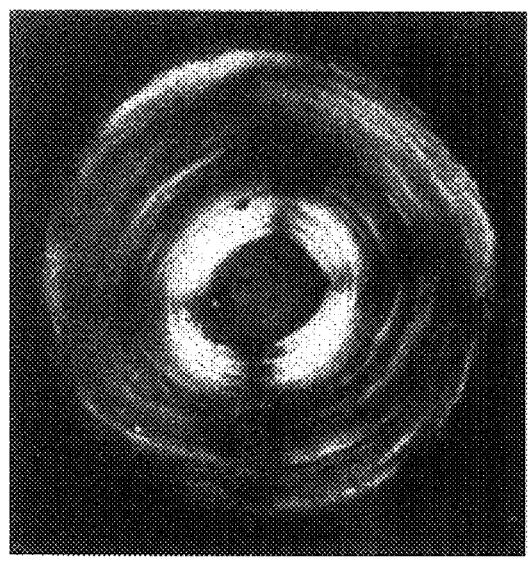
FIGS. 4(a)–(c). (a) Cross section of an isolated longitudinal osteon, magnified 270 times. (b) Cross section of an isolated alternate osteon, magnified 270 times. (c) An isolated osteonic sample with lugs, magnified 20 times. Lugs are used to grab the sample during mechanical testing. Dimensions: inner diameter 52 μm, outer diameter 225 μm, length 500 μm.
Figure 4B:
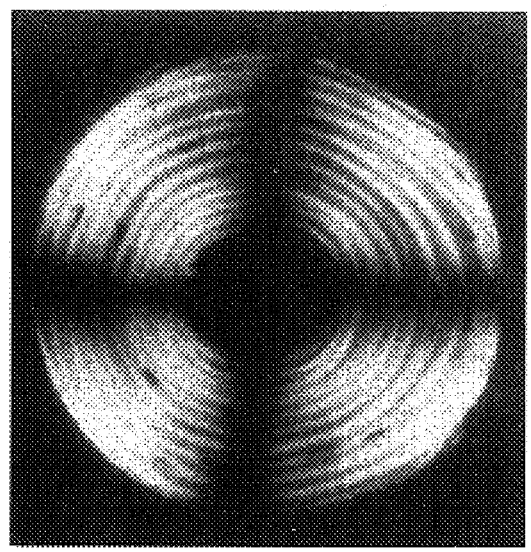

Sample preparation and selection in this example will be achieved by applying the Ascenzi A. et al. (1994) methodology. Accurate sample preparation is important, and the Ascenzi method is preferred. The femoral shafts of human corpses free from evident skeletal faults will provide the bone material for the study. Longitudinal shaft segments about 30 mm long will be first sawn off, and longitudinal sections slightly thicker than an osteon (350 µm) will then be prepared using a Leitz rotating-saw microtome. A continuous water-spout will be incorporated to prevent any overheating of the material. Osteon samples will then be isolated from the sections. The features determining sample selection will be the degree of calcification and the orientation of the collagen bundles and crystallites. Microradiographic examination, preferably according to Amprino and Engstrom (1952), will allow the selection of fully calcified osteon samples. Two types of osteons will be selected. They correspond to two different collagen bundle patterns in fiber orientation in successive lamellae. Under the polarizing microscope, one type, the longitudinal osteon, has a predominantly dark appearance in cross section (FIG. 4a); whereas the other type, the alternate osteon, reveals alternately bright and dark lamellae (FIG. 4b).

When bone sections are cut longitudinally, the two osteon types are easy to recognize provided that the thickness of the sections is much less than the diameter of an osteon. Longitudinal osteons appear to be almost uniformly bright under the polarizing microscope, while alternate osteons show alternatively bright and dark lamellae. When the thickness of the bone section differs little from the mean diameter of the osteon, concentric lamellae overlap, thereby reducing or precluding the visibility of dark lamellae, and leaving open the possibility that an alternate osteon may have a bright appearance. As a result, identification only becomes certain once a cross section has been cut from the osteon using a microscopic drill (Ascenzi A. et al., 1994). Hence, cyclic loading must be performed before undertaking positive identification of the osteon type.

With reference to the position and orientation of the haversian canal, it is necessary that the canal lie midway between the surface of the cylindrical sample and parallel to it, so that torsion is applied around the osteon axis. This calls for the preliminary separation of the osteon sample, e.g. by application of a technique described below. This technique allows the position and orientation of the canal to be calculated by measuring its distance from the outer surface of the sample at various levels and rotational angles.

The samples are isolated in two stages. During the first stage the sample, consisting of the central portion of an osteon, 500 µm in length, with the ends penetrating into two rectangular lugs, is separated from the bone section using a device as described in Ascenzi A. and Bonucci (1968) and Ascenzi A. (1990). As isolation of the central portion of the osteon is achieved by drilling, its section has a coarse, square shape. During the second stage, a micro-grinding lathe is used to give the central portion a cylindrical form, with the haversian canal running through it axially. The lathe to be used was designed and developed by the CECOM Company and is described by Ascenzi A. et al. (1994). The device grinds the sample by a minute steel blade whose edge, 500 µm long, is equal to the length of a coarsely isolated sample. The forward and backward movements of the blade are monitored by a micrometer. The length and other dimensions of the various samples were kept virtually constant; one criterion for the choice of the samples is that their haversian canal measures 40±3 µm in diameter. Additionally, a stopper controls the forward and backward movement of the steel blade on the micro-grinding lathe to provide a series of samples whose external diameter equals 210±3 µm. This provides a precise comparison of samples' torsional properties (Ascenzi A. et al., 1990). Osteons are not uniform in dimensions. With the dimensions carefully controlled and standardized to exclude defects and other structures, the material rather than structural properties are determined for the osteons. This information can then be applied to osteonal structures of varying dimensions under the assumption of homogeneity at the level of the osteon rather than for the macroscopic specimen.

The relative dimensions of the osteon samples may not appear to conform to those conventionally suggested for material testing. They reflect conditions made necessary by the distinctive nature of bone microstructure. In particular, 500 µm is the maximum length compatible with the avoidance of Volkmann's canals in the wall of the specimen. An external diameter of 210 µm is the maximum dimension possible that ensures that portions of the neighboring structures are not included in the sample as a result of irregularities in the thickness of an osteon. The internal diameter of fully calcified osteons averages 40 µm.

Figure 4C:
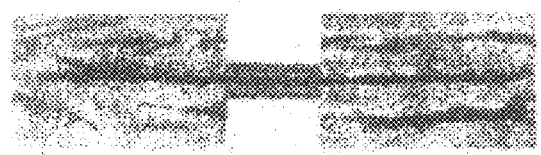

FIG. 4c shows a completely isolated osteon sample held within rectangular lugs. The lugs allow the sample to be firmly attached to the device while hysteretic loops are recorded. The central portion of each sample will be only 500 µm long; consequently, the sample will not include Volkmann's canals which would behave as discontinuities. In addition, the osteon sample selection criteria includes that the vascular canal should run strictly parallel to and equidistant from the surface of the cylindrical sample and that there should not be small surface defects. The canal's position and orientation are assessed by checking the distance between vascular canal and external surface of sample at various rotational angles and levels. To exclude the presence of small surface defects that could alter the shear modulus values in torsional testing, each sample is subjected to careful optical microscope examination. Severe criteria are set for osteon sample selection. Osteon types can only be identified from a prepared cross section only after a sample has been tested. This means that to obtain 60 samples divided between those containing longitudinal and alternate osteons, which satisfactorily complete the procedures adopted for the recording of the hysteretic loops under torsion, it will be necessary to prepare between 800 and 1,000 samples.

Figure 10:
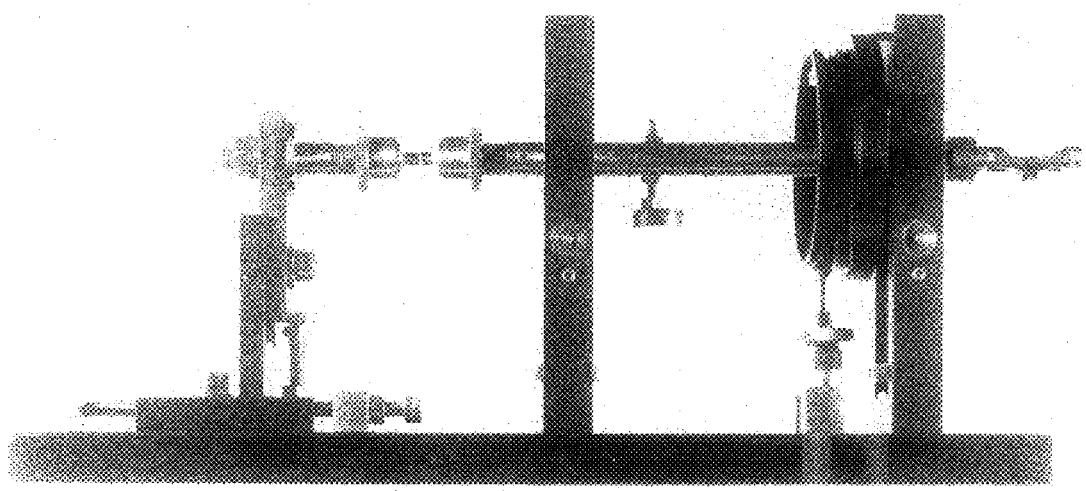
FIG. 10. Shows a device for subjecting bone to torsional cyclical loading.
Figure 11:
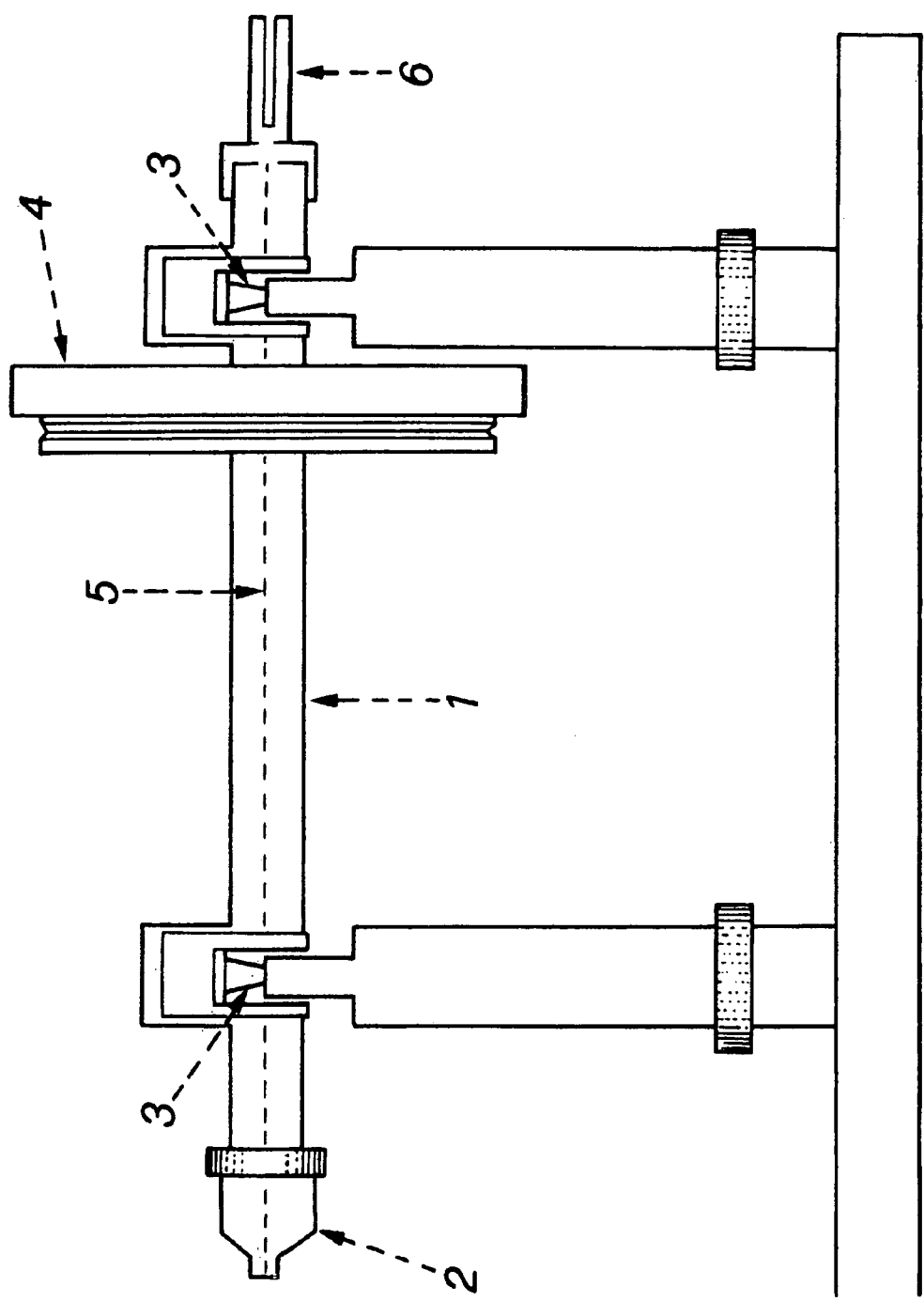
FIG. 11. A schematic diagram of a device for subjecting bone to torsional cyclical loading, where (1) is a rotational axis with jaws; (2) and (3) are hard metal wedges of a pendulum loading system; (4) is a wheel around which a tungsten thread loaded with weights is attached; (5) is the axis of the pendulum; and (6) is a mirror.

The apparatus is an adaptation of the device for testing osteons under torsion to failure described in Ascenzi A. et al., 1994), and further described in FIGS. 10 and 11. This device consists of a rotational axis, point (1) in FIG. 11, with two sets of jaws, point (2) in FIG. 11, which grip the specimen during testing. The jaws are oriented along the same axis but none of them are free to move axially. This sets up an axial loading effect, which could influence absolute measurements but may be neglected when, as in this investigation, comparative measurements are considered.

One set of jaws is fixed, while the other turns in synchrony with a wheel, point (4) in FIG. 11, measuring 61 mm in diameter. In order to minimize the rotating friction of the turning jaw, a pendulum loading system is adopted. The axis of the pendulum loading system is indicated as point (5) in FIG. 11. The frictionless fulcrum of the pendulum loading system is the tip of a hard metal wedge, point (3) in FIG. 11. The maximum oscillation of the pendulum is fixed at 55°. A tungsten thread, whose section measures 20 μm in diameter, winds around the rim of the wheel as a series of 0.1 gram weights is attached incrementally at one end of the tungsten thread. Weights are added one by one until failure occurs for monotonic torsional loading. The load limit is chosen so that the corresponding torque is approximately equal to the middle value between the maximum possible elastic torque and fully plastic torque. Preliminary trials indicate a load limit of 0.9–1.0 gram for fully calcified longitudinal osteons and of 0.8–0.9 gram from fully calcified alternate osteons and of 0.6–0.7 gram for decalcified longitudinal osteons and of 0.5–0.6 gram from decalcified alternate osteons. Once the load limit is reached, the weights will be detached one by one. The procedure will then be repeated at the other end of the tungsten thread. In this way, the osteon specimen rigidly clamped at one end is progressively twisted at the other end by a torque in counterclockwise and clockwise directions alternatively, so as to achieving cyclic loading. The interval between the application of two consecutive weights will be kept constant at 4 sec. A stereoscopic microscope will be used to verify that the axis around which torsion occurs coincides with the osteon axis. The aim of this operation is to check that the center of each jaw corresponds to one end of the osteon sample canal. The angle through which one end of the specimen twists relative to the other during testing is measured by applying an optical method based on the reflection of a laser beam from a small mirror attached to the rotating set of jaws. The variations in the angle of twist are read on a graduated scale placed 160 cm from the device. The precision and accuracy of the graduated scale coincide with those of the apparatus, as checked by applying experimental procedures. Because the diagrams obtained when testing begins in the counterclockwise (or positive) direction should look essentially like the diagrams obtained when testing begins in the clockwise (or negative) direction, all the diagrams will be recorded starting in the counterclockwise direction, according to the standard practice reported in the literature.

The cycles applied to each specimen will vary in number and they will be interrupted before the spontaneous sample rupture. Preliminary specimen testing taken to rupture gives an indication of the angle-of-twist values at rupture and therefore give an indication to stop cycling when angle-of-twist values get close to the preliminary rupture values. The final cycle will therefore be interpreted as the cycle preceding the interruption of the experiment; in consequence, it has no physical meaning. Issues related to osteon fatigue-life will not be part of this study because they require the ultimate destruction of the specimen which would prevent the ability to properly identify the sample after cyclic loading. Interruption of the experiment prior to rupture is necessary because, as previously noted, the osteon type can only be identified with certainty by preparation of a cross-section before rupture, but after testing. Before preparation of the cross-section for identification, samples will be examined under the optical microscope to analyze the nature and size of lesions. Osteon samples are examined under an optical microscope as whole, even though to do so samples need to be removed from the torsion device; such removal can cause structural changes, e.g. partial closure of cracks. The nature of fatigue-damage cannot be verified directly under microscope. In fact, fractures due to cycling and those due to osteon sawing to produce the section are not distinguishable. There is no universally accepted technique available to allow qualitative observation of fatigue-damage. The only experimental alternative is x-ray diffraction, which provides only quantitative indication of fatigue-damage (Ascenzi A. et al., 1998).

Of 60 osteon samples, 7 longitudinal and 7 alternate osteon samples will be decalcified by treatment in a versene solution buffered to pH 7 (Ascenzi A. et al., 1967). Measuring the increase in birefringence at regular intervals of time will check the decalcification (Ascenzi A. and Bonucci, 1964). After hydration of the material with saline solution, 20 longitudinal and 20 alternate fully calcified osteon samples, and the 7 longitudinal and 7 alternate decalcified osteon samples will be tested wet as described above. The remaining 6 osteons will be tested on the first and second cycles only and their dimensions will be measured (by means of a micrometer under an optical microscope) after cycling and before the sectional cutting for osteon type determination. The mechanical testing will be conducted at 20° C. The specimens will be maintained wet during testing by continuous use of a micropipette.

Upon completion of the experimental portion of the research, hysteretic values of torque vs. angle of twist will be plotted for each osteon sample.

The proposed mechanical testing is performed quasi-statically so rate dependencies are not expected in the material response. To confirm this, a series of twist and hold experiments will be performed as a preliminary test to see if significant strain relaxation (creep) occurs in the time frame that it takes to complete an experimental cycle. The presence of creep would manifest itself by maintenance of the shape of the curve but with a clear translation of the entire hysteresis loop. If creep is not present, the area under the hysteresis loop is the energy absorption. If creep is present, it will be accounted for by the addition of viscoelastic terms.

B. Mathematical Analysis of Hysteretic Curves

To establish analogies and differences among plots, the characteristics of torque vs. angle of twist plots are quantified by means of a polynomial approximation for each half-cycle. (Shiga et al., 1970; Ascenzi A. et al., 1997).

Measurements and Plots a) Least-square regression will be applied to the data for each half-cycle to identify the best polynomial approximation of at least second order. The degree cannot be 1 because the half-cycle involves the inelastic range which is characteristically nonlinear.

b) The goodness of the approximation will be determined through analysis of the residuals and computation of the percent variation in torque explained by the regression. A lower bound for $r^2$ is set to 0.98. The degree of the polynomial approximation at (a) will be increased in a stepwise fashion until a good-approximation is found for all half-cycles.

c) Let n be the smallest integer for which there is a good-approximating polynomial for all half-cycles. Let the polynomial equation be $$y(x) = \sum_{i=o}^{n} a_i x^i.$$

Note that such an equation does not include symbolism that denotes the half-cycle; this is done to add clarity and does not lead to confusion. A literature search suggests that n might equal 3 or 4 (Shiga et al., 1970 and Ascenzi et al., 1997a). Each coefficient $a_i$ for any given cycle will be plotted with respect to the maximum angle-of-twist on that cycle, for negative and positive torque half-cycles separately for each osteon type, to visualize the value's variation as the number of cycles increases.

d) The first derivative of the polynomial, $$y'(x) = \sum_{i=o}^{n} i a_i x^{(i-1)},$$

will be taken to represent the stiffness of each individual half cycle.

e) Compute relative extrema of y'(x) on each half-cycle. Because of increasing structural damage, stiffness is generally either always decreasing on both negative and positive torque half-cycles or it shows a sharp change from decreasing to increasing only once on each half-cycle. Therefore, y'(x) should show no relative maximum and a marked relative minimum. If such relative minimum exists, the graph of y(x) shows an inflection point, i.e. pinching is present. Let $h_m$ and $k_m$ denote twist and torque values at the stiffness relative minimum of the half-cycle. In these notations, $y'(h_m)$ denotes the minimum value of stiffness.

f) Compute $y'(x_b)$ and $y'(x_e)$, the stiffness at the begin and at the end of each cycle.

g) Compute the absolute maximum of the function $|y''(x)|/(1+(y'(x))2)3/2$ on any given half-cycle. This is the maximum curvature per half-cycle and will be denoted by $m_c$.

h) Compute the difference between the integral of y(x) over the first half-cycle and the integral of y(x) over the second half-cycle. Such value approximates the area of the region bounded by the first cycle. This is the energy absorption during the first cycle and will be denoted $e_1$.

Differences in hysteretic behavior between longitudinal and alternate osteons will be established by studying the distributions of maximum twist, $h_m$, $k_m$, $y'(h_m)$, $y'(x_b)-y'(x_e)$, $m_c$, and $e_1$ computed above. The statistical t-test, paired or unpaired, will be applied on means of distribution or on the mean of the distribution's logarithm if the distribution is not normal.

The mean of the differences of twist limits between the last and first cycle obtained from the experimental diagram will be computed. It will be compared between negative and positive torque half-cycles for longitudinal and for alternate osteons, separately. The magnitude of such value should be smaller for longitudinal osteons than alternating osteons because longitudinal osteons resist torsion better than alternate osteons.

The signs of $h_m$ (and $k_m$, respectively) at the first and last cycle will be analyzed. $h_m$ (and $k_m$, respectively) should have the same sign for the two osteon type separately, up to possibly a few samples. This would indicate that the twist at minimum stiffness should not change much at all within all negative and positive torque half-cycles separately, for both osteon types. This would be in agreement with the tight and well organized osteon structure.

A paired two-sample t-test will be applied to the means of the values of $h_m$ (and $k_m$, respectively) at each of the cycles in any given set of corresponding cycles of the two osteon types. This compares the values of minimum twist (and torque, respectively) for negative and positive torque half-cycles.

A paired two-sample t-test will be applied to the means of $y'(h_m)$ and the coefficients of y'(x) for the two osteon types, separately at each of the cycles in any given set of corresponding cycles of hysteretic diagrams. This compares the minimum value of the stiffness between the negative and positive torque half-cycles.

An unpaired two-sample t-test will be applied to the means of $h_m$ (and $k_m$, respectively) for the two osteon types at each of the cycles in any given set of corresponding cycles of hysteretic diagrams. This will compare the values of twist (and torque, respectively) at the inflection point for the two osteon types.

A unpaired two-sample t-test will be applied to the means of $y'(h_b)-y'(h_e)$ for the two osteon types at each of the cycles. This will compare the stiffness decrease within a given cycle between the two osteon types.

A paired t-test will be used on the mean of the difference of $m_c$ for negative and positive torque half-cycles at each of the cycles in any given set of corresponding cycles of hysteretic diagrams. This will compare the maximum value of the curvature of the stress-twist diagram between negative and positive torque half-cycles, for the two osteon types, separately. The maximum value of curvature of the torque-twist diagram is expected to be larger on the positive than negative torque half-cycle for longitudinal osteons; whereas, the maximum values of the curvature of the torque-twist diagram under negative and positive torque half-cycle for alternate osteons should show no difference. As a consequence of the reduced stiffness the energy absorption should be larger for longitudinal than for alternate osteons.

A paired t-test will be used on the difference of the means of each coefficient $a_i$ of y' at last and first cycles, on both negative and positive torque half-cycles, separately. For both osteon types, the value of y' is expected to decrease from the first to the last cycle on both negative and positive torque half-cycles for any value of the twist x. This test will measure stiffness degradation here defined as the decreasing of stiffness at any given twist value on either a negative or positive torque half-cycle as the number of cycles increases.

The existence of the value $h_m$ shows the S-shape of the half-cycles that identifies pinching. Pinching is expected to be present for each cycle for both types of osteon. If pinching is present, pinching degradation will be computed.

A paired two-sample t-test will be applied to the means of $y'(h_m)$ for the two half-cycles of any given cycle. This compares pinching degradation for the two osteon types separately. Pinching degradation at any cycle is the reduction in stiffness from its value at the deflection point of the negative torque half-cycle to a lesser value at the deflection point of the positive torque half-cycle.

An unpaired two-sample t-test on the means of the value of minimum stiffness $y'(h_m)$ for longitudinal and alternate osteons at any given half cycle. This compares pinching degradation between the two osteon types.

An unpaired two-sample t-test will be applied to the means of $e_1$ for longitudinal and alternate osteons. This compares energy absorption between the two osteon types at each of the cycles in any given set of corresponding cycles of hysteretic diagrams.

The mechanical meaning of some of the parameters used in the above analysis of experimental diagrams (e.g. stiffness, energy absorption) will be made clear as such parameters will be correlated to ultrastructural behavior during fracture propagation in the model described at section IV. Up to this point they are comparative measures of behavior between longitudinal and alternate osteons under torsional loading.

C. Interpretation

A structural and biological interpretation of the shape of torsional hysteretic loops in osteons through the results of the previous steps uses a segment representation of each cycle of the curvilinear recorded diagram.

If, as it is anticipated, pinching exists, the bilinear model of FIG. 12 is appropriate. Here points B and E approximate endpoints of the negative torque half-cycle, while points E and H approximate endpoints of the positive torque half-cycle; segments DC and FG approximate tangent lines to the curves at the inflection points. The three segments modeling the twist decreasing branch show that stiffness decreases (along segments BC and CU) to a minimum value and then increases (along segments UD and DE). Similarly, the three segments modeling the positive torque half-cycle show that stiffness decreases (along segments EF and FL) to a minimum value and then increases (along segments LG and GH).

The slope of segment DC on the negative (FG on the positive, respectively) torque side of the bilinear model is smaller than both the slopes of segments ED and CB (EF and GH, respectively) and therefore responsible for a contraction of the cycle that constitutes pinching. The existence of pinching resides in the torque-angle-of-twist branch AB of the primary curve, where lesions appear as a result of yielding of components of the bone matrix under load as the angle-of twist increases to the right. Reversal of loading is required to close the lesions; this will occur once the minimum angle-of-twist of the unloading portion BC of the curve is exceeded. Once point C is passed, stiffness, as negative torque is decreasing, shows a progressive, slight, unsteady increase to point D. The lesions are then repaired and stiffness rises steadily to point E.

The opposite will occur at the diagram portions marked EF, FG, and GH. After passing the minimum angle-of-twist of the unloading portion (EF), progressive resolution of the damaged structural components will occur, leading to a slight, unsteady increase in stiffness as negative torque increases (FG). After point G, stiffness will increase steadily to point H, as negative torque increases. In particular, pinching would correspond to segment CD on the negative torque side, where repair of the lesions occurs, and to segment FG on the positive torque side, where resolution of the lesions occurs. This explanation, in which lesions form on the negative torque half-cycle and reinforcements yield on the positive torque half-cycle, does not take into account buckling. If buckling occurs, the situation is reversed: lesions form on the positive torque half-cycle and reinforcements yield on the negative torque half-cycle.

If pinching does not exist, there is no contraction along the cycle. In this case, the slope of segment DC on the negative (FG on the positive, respectively) torque side of the model lies in between the values of the slopes of ED and CB (EF and GH, respectively), as depicted in FIG. 12b. The slope of the segments modeling the cycle shows that stiffness decreases along all of them; which might mean that lesions do not repair and do not resolve as they would with pinching. In this scenario it is reasonable to assume that torsional loading creates lesions distributed in a more disorderly fashion in the osteon than in tensile-compressive loading (aligned with longitudinal bundles and where pinching is present). Before load reversal, the hydroxyapatite crystallites might have detached and cracked in a way that the original alignment is destroyed. In this case a partial realignment does not occur later along the first half-cycle as to bring an increase in stiffness. Consequently, there are no lesions to resolve during the successive half-cycle and stiffness would keep decreasing. This explanation, in which lesions form on the negative torque half-cycle and reinforcements yield on the positive torque half-cycle, does not take into account buckling. If buckling occurs, the situation is reversed. Before load reversal, collagen bundles might yield in a way that loses track of the original alignment. Similarly this does not allow even a partial realignment to take place later along the first half-cycle, after lesions involving the cracking of hydroxyapatite have occurred, so as to increase stiffness. Consequently, no partial alignment of bundles could be restored before bundles start yielding during the successive half-cycle and stiffness would keep decreasing. Such interpretation, where lack of hydroxyapatite crystallite alignment is greater under torsional cyclic loading than tension-compression cyclic loading, could be verified additionally by means of X-ray diffraction (Ascenzi A. et al., 1998).

Figure 12A:
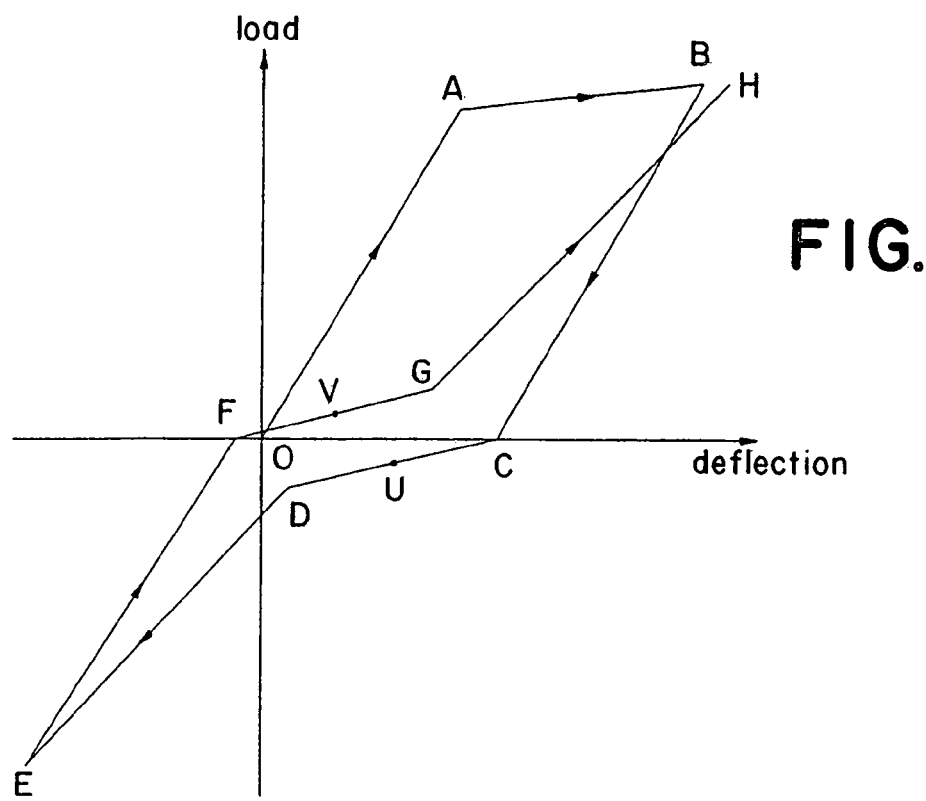
FIG. 12. An idealized bilinear hysteresis model of curve prior to cycling and a first cycling loop, where (a) pinching is present; and (b) pinching is not present.
Figure 12B:
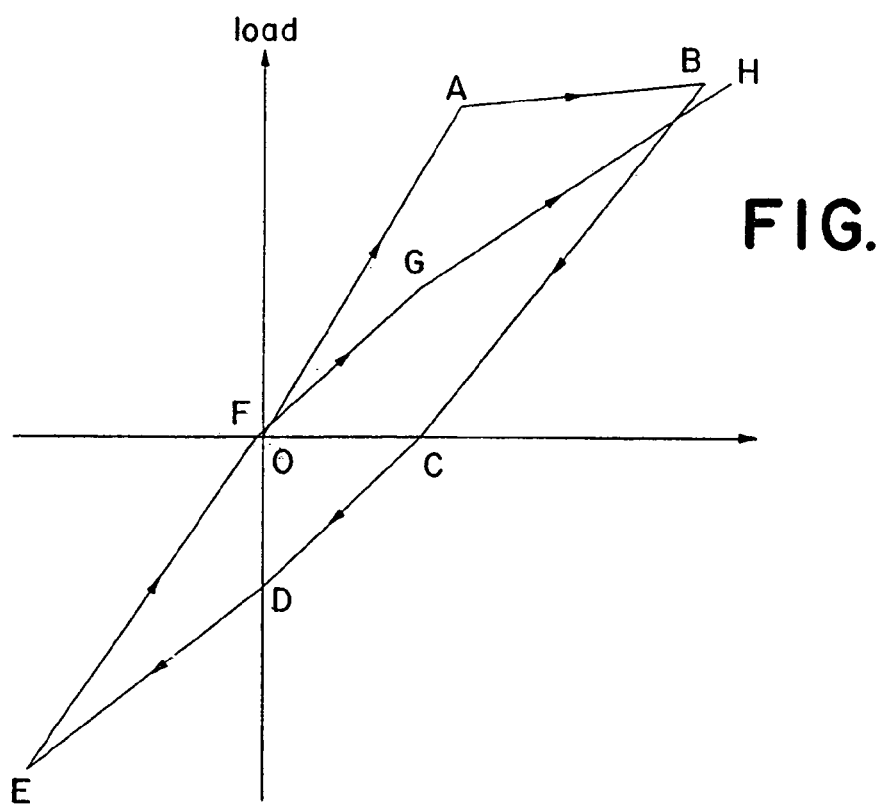

The results of the measurements and plots above will give the positions and inclinations of the segments in FIG. 12. For instance, the t-test on the means of $k_m$ along the first half-cycle for longitudinal and alternate osteons is expected to indicate that $k_m$ is significantly higher for alternate osteon. This means that point U in FIG. 12a is higher for alternate osteons, that is, cracks close and stiffness switches start increasing for a smaller torque value. This is consistent with the more complex structure of alternate osteons.

D. Fracture Model

/The purpose of the fracture model is to show that cumulative micro-cracking, de-bonding, void growth and fiber breakage associated with repeated loading of osteons causes a progressive loss of stiffness and pinching, and increase of energy absorption. The lesions observed under an optical microscope in osteon samples subjected to cyclic torsional loading will serve to develop osteon models and to formulate biological hypotheses on propagation of fractures. The fracture model will be based on:

hypotheses on ultrastructural components' behavior under cyclic torsional loading formulated from the experimental hysteretic plots;

ultrastructural components' mechanical properties;

fractures observed in osteons during monotonic torsional loading; and fractures observed in macroscopic bone specimens.

This aspect of the model is an adaptation and extension of the approach of Gupta and Bergstrom (1998). The fracture propagation model is a micromechanical bone model that allows prediction of the progressive growth of faulting zones, by considering the increased stress experienced in the vicinity of an already highly cracked region. The nucleation of initial damage is determined by the assessment of the points more susceptible to fracture. The progressive growth of the fault nucleus is considered in a statistical manner by the use of stress enhancement factors, which address the increased probability of failure in the vicinity of regions that are already cracked.

The geometric model of each of the longitudinal and alternate osteon samples before mechanical testing consists of a hollow cylinder with coaxial lateral surfaces. Its internal diameter, external diameter, and height equal 40 µm, 210 µm, and 500 µm, respectively. Each such hollow cylinder presents voids, and about 20% of each such hollow cylinder consists of voids (Piekarski, 1970) which model canaliculae and lacunae.

The material model of each of the longitudinal and alternate osteon samples before mechanical testing consists of a laminate whose length, width, and height correspond to cylindrical shell circumference, thickness, and height, respectively (FIG. 9a). The layers are unidirectional fiber-reinforced laminae (FIG. 9b) of the same matrix and fibers. The matrix and fibers are each treated as homogeneous and isotropic. The fibers are assumed to be circular in cross-section with a diameter of 800 Å, randomly distributed in the transverse plane and perfectly embedded in matrix. The lamina with fiber inclination γ is named γ-lamina. The elastic properties of matrix and fibers model the elastic properties of hydroxyapatite (Katz and Ukraincik, 1971) and collagen (Currey, 1969). The matrix occupies 40% of the lamina volume without voids (Bonfield and Li, 1967). The matrix (fiber, respectively) volume decreases (increases, respectively) slightly from inner to outer lamina (Amprino and Engstrom, 1952; Rho et al., 1999).

The longitudinal osteon model consists of 9 longitudinal lamellae of the same thickness. Longitudinal lamellae are modeled by alternating +82-laminae and −82-laminae (Frasca et al., 1977). The alternate osteon model consists of 7 transverse lamellae with 5 longitudinal lamellae layered between them (Giraude-Gille, 1988). The transverse lamella is modeled by the laminar sequence [−61.5, −41, −20.5, 0, 20.5, 41, 61.5] (Ascenzi M.-G., 1999b). This sequence is subjected to prestress as described in Ascenzi M.-G., 1998a and 1999b. A longitudinal lamellar model is 9.45 μm thick and a transverse lamellar model is 5.40 μm thick (e.g. Gebhardt, 1906; Ziv et al., 1996). The matrix volume is 10% higher in the longitudinal lamellar model than it is in the the transverse lamellar model (Marotti et al., 1994).

E. Bone Structure Simulation

To model fracture propagation in osteons, each of the longitudinal and alternate osteon models is divided into a discrete number of elements, e.g. 618,317. The element mesh will be refined to achieve a convergent solution. A computer simulation program, such as a Monte Carlo simulation, will be used to do the following tasks.

1. For any given value of torque applied to experimental samples, the distribution of stress in the osteon model is computed. Such computation will take into account voids.
2. Such stress distribution will be added to the distribution of prestress.
3. The strain associated to the resulting stress will be computed on each phase within each element.
4. From the strain associated to the resulting stress, the overall deformation of the hollow cylindrical shell will be computed.
5. From the strain in each phase within each element, the phase deformation will be computed.
6. The strain in each phase within each element is compared to the yield strain.
7. The strain is chosen as the criterion for osteon failure (Piekarski, 1970). The maximum strain, called critical strain, after which fracture occurs within each phase is provided by the literature. Perfect bonding at the interface between phases is assumed unless experimentally observed cracks appear to initiate at this interface. If that is the case, a failure criterion (e.g. Von Mises) will be included.
8. The elastic properties of fractured phases will be computed by means of formulas of the type $E_f=E_e/(1+(1+vv_e)(k_e\lambda)/2)$ (Gupta and Bergstrom, 1998).
9. The element is declared broken if all phases in that element have failed.
10. The elements are assumed to be aligned in independent rows such that the problem of fracture propagation becomes one dimensional.
11. To model the progressive growth of damage, the torque will be increased incrementally, and using the fracture criterion above, the number of failure elements will be established.
12. The increased probability of fracture in the neighborhood of an already fractured element will be considered using the concept of stress enhancement factors.
13. If all elements on one row are broken, the strain level at which all elements on one row are broken is taken as the failure strain for that row. The process is repeated for each row in the model. Once the maximum torque is reached, the program stops.
14. At this point, the simulation of fracture propagation before the first hysteretic half-cycle is completed.
15. The program incrementally applies a clockwise torque decreasingly to the maximum torque applied experimentally to samples, and at each increment it repeats steps 2 and 3 above, so as to complete the failure simulation during the first half-cycle of the first cycle.
16. Step 15 is repeated for the corresponding counterclockwise torque so as to complete the fracture simulation during the second half cycle of the first cycle.
17. The fractures obtained according to the model should be comparable with those observed in osteon samples submitted to one cycle only.
18. The fracture simulation sequence is repeated through the last cycle.
19. Fracture simulation is repeated further, as desired. Fractures obtained in this way, according to the model, should be compatible with those observed in cycled osteon samples at the last cycle.

F. Results

Entities computed from the experimental hysteretic diagrams, such as stiffness degradation, pinching degradation and increase in energy absorption, up to the second cycle, correlate with the fracture propagation of the fracture model.

The same geometric/material models and computer program will be used to simulate fracture propagation under tension, compression, and shear, separately. The resulting fractures will match the fractures observed in osteon propagation under tension, compression, and shear respectively (Ascenzi A. and Bonucci, 1967 and 1968; Ascenzi A. et al., 1972).

Predictions and phenomena simulated according to the model of the invention include that in both osteon types, a fracture starts at a weaker point of the bone structure (Carter et al., 1981), at the weak interfaces between two outer lamellae (e.g. Piekarski, 1970), presumably because of the hydroxyapatite decrease in osteons from vascular canal to outer wall (Rho et al., 1999).

In longitudinal osteons, the fracture starts somewhat longitudinally, between collagen bundles. It then deviates once or twice at the beginning of the fracture and is soon followed by a smooth crack advancing rapidly across the osteon to possibly end in the vascular canal. As cycling continues, collagen bundles between cracks break, and cracks join to create one or more long almost vertical cracks.

In alternate osteons, cracks are expected to spread obliquely by following the weak interfaces of lamellae. The transverse and oblique collagen bundles may break before the longitudinal ones as the osteon section enlarges. Cracks spread through lamellae less rapidly than in longitudinal osteons as explained by the crack propagation control, characteristic of composite materials (Cook and Gordon, 1964). Once the crack breaks through transverse and oblique bundles, it will propagate faster straight through the vascular canal. A long crack should show an oblique orientation between upper and lower extremities.

It follows, unexpectedly, that the longitudinal osteon is weaker in longitudinal than in transverse shearing, while expectedly the alternate osteon is weaker in tension than in shear (Ascenzi et al., 1967 and 1972). This is because when a torque is applied to a body, tensile and compressive stresses are produced on the lateral surface and torsional shearing stresses are produced on the cross-section of the body. The tensile and compressive stresses act approximately at a 45° angle to the long axis of the body. The direction of the shearing stress on the cross-section of the body is the same as that of the force producing torsion. If a material is weaker in longitudinal than in transverse shearing, the first cracks arise from axial shearing stresses and appear in a longitudinal direction. However, if the material is weaker in tension than in shear, it usually cracks along a spiral course inclined at a 45° angle to the long axis of the body. The reason for this is that a state of pure shear is equivalent to a state of tension in one direction and of compression in the opposite direction (Timoshenko and Young, 1962). The tension stress produces a spiral crack in the body.

For both osteon types 3 to 4 small cracks form in the hydroxyapatite and collagen, which yields and pulls and/or buckles and makes the cracks spread within lamellae. Microcracks form ahead of the advancing fracture line. Afterwards, during torque reversal, width of cracks and deformation decrease. Collagen may buckle and some resisting strength may appear at zero torque. As cycling continues, cracks extend through the lamellae and join.

The slow propagation of cracks in the areas containing transverse and oblique collagen bundles allows for the area to absorb a large amount of energy. Slow propagation is essentially a pull-out type mechanism, that is, hydroxyapatite crystallites are pulled out of the collagen by shear failure at the fiber-matrix interface. The rapid propagation of cracks in areas containing approximately vertical collagen bundles allows very low energy absorption. This should be compatible with larger areas enclosed by cycles of experimental plots of alternate osteons (see last t-test in Sec. A above).

Hydroxyapatite crystallites are pulled out from collagen around canaliculae.

At low strain rates in compression distortion of the lamellar structures occurs (McElhaney and Byars, 1965).

The propagating crack generally has the tendency to avoid discontinuities (Piekarsly, 1970), hence increasing its length. Discontinuities act as crack arresters by blunting the tip of the crack which enters them.

The fracture model is expected to agree with fractures observed in osteons cycled only for first and second complete cycle. The dimensions of the hollow cylindrical model after one cycle, two cycles, and the last cycle of torsional loading should match the means of the osteon samples' dimensions measured experimentally. Furthermore, the role of the models' fibers is expected to check with the cyclic behavior of decalcified osteons.

The sudden shift of the osteon shape (FIG. 4) from a circular to a square cross-section suggests a stress concentration at the lugs. Therefore, fractures may begin at the end of some samples earlier during loading than would otherwise be expected.

Lamellar thickness and width were measured on 20 bright and 20 extinct peripheral lamellar samples in quintuplicate in dry osteon samples by Delta Sistemi IAS 2000 image analysis system, and again after wetting with a micropipette. This table shows means and standard deviations. Thinner extinct lamellae were used for comparison with bright lamellae. It is known that extinct lamellae are thicker than bright ones, whether dry or wet. The Student t-test is run on the data to determine statistical differences between dry and wet lamellar dimensions.

| Sample | Thickness Dry | Thickness Wet | Width dry | Width wet |
|---|---|---|---|---|
| Bright | 3.30 ± 0.88 | 3.56 ± 0.93 | 70.30 ± 9.28 | 72.45 ± 9.58 |
| Extinct | 4.13 ± 1.23 | 34.10 ± 1.10 | 70.30 ± 9.28 | 72.45 ± 9.58 |

Whether dry or wet, bright lamellae are significantly thinner than extinct lamellae when enclosed in alternate osteons (this agrees with previous results, e.g., Rho et al., 1999). Additionally, wet and dry conditions affect bright and extinct lamella thickness differently. Bright lamellae are significantly less thick when dry than wet. In contrast, extinct lamellae thickness remains constant whether wet or dry.

The bright lamella thickness increases from dry to wet which may be due to the higher quota of mucopolysaccarides, which expand with water, and to the transverse collagen bundles in the bright lamella tightly encircling extinct lamella, thereby impeding expansion. Height of both bright and extinct lamellae is significantly smaller when dry. In addition, the thickness along lower and upper borders shows variations up to 50–60%. This will be included in the model. Width variation is very low.

The model provides an advantageously simplified simulation or representation of osteon structure. For example, partially calcified collagen bundles are excluded from the model. The model provides a useful and improved description of bone structure and mechanics, even though the shape and dimensions of hydroxyapatite crystallites and the relationship of these parameters to the organic components of the matrix are only partially known. Not all collagen bundles are completely calcified. Those, which are note calcified take up crystallites only on 400 A bands (Ascenzi, A. et al., 1965). Such bundles may be comprised of relative more stiff 400 A bands separated by relatively more flexible decalcified collagen segments. In a preferred embodiment of the invention, partially calcified collagen bundles are not modeled, in favor of modeling fibers in uncalcified collagen bundles. The matrix, which models the hydroxyapatite crystals, lies outside the fibers. Pinching is incorporated into the model is related to the yielding and bucking of fibers, and provides an approximation of the yielding and buckling of partially calcified collagen bundles. In preferred embodiments, fracture propagation is modeled and cracks will tend to propagate before buckling is likely to occur, because the model in most cases assumes that individual fibers are perfectly bonded to and are uniformly supported by the matrix. The model also excludes complex consideration of pore fluids in preferred embodiments which balance relative simplicity with achieving a reliable and accurate bone model.

The patents, applications, test methods, and publications mentioned herein are hereby incorporated by reference in their entirety.

Many variations of the present invention will suggest themselves to those skilled in the art in light of the above detailed description. All such obvious variations are within the fill intended scope of the appended claims.

BIBLIOGRAPHY

Amprino, R. and Engström, A. (1952) Studies on X-ray absorption and diffraction of bone tissue. Acta Anat, 15, 1–22.

Antman, S. (1995) Nonlinear Problems of Elasticity. Springer. New York

Ascenzi, A. (1988) The micromechanics versus the macromechanics of cortical bone—A comprehensive presentation. J. Biomech. Eng., 110, 357–363.

Ascenzi, A., Ascenzi, M.-G., and Benvenuti, A. (in preparation, 2000) The revisited osteon.

Ascenzi, A., Ascenzi M. G., Benvenuti, A., and Mango, F. (1997) Pinching in longitudinal and alternate osteons during cyclic loading. J. Biomechanics, 30, 689–695.

Ascenzi, A., Baschieri P., and Benvenuti, A. (1994) The torsional properties of single selected osteons. J. Biomech., 27, 875–884.

Ascenzi, A., Baschieri P., and Benvenuti, A. (1990) The bending properties of single osteons. J. Biornech., 23, 763771.

Ascenzi, A. and Benvenuti, A., Evidence of a state of initial stress in osteonic lamellae, Acta Orthop. Belg., 46, 580, 1980.

Ascenzi, A., Benvenuti, A., Mango, F. and Simili, R. (1985) Mechanical hysteresis loops from single osteons: Technical devices and preliminary results. J. Biomech., 18, 391–398.

Ascenzi, A., Benvenuti, A., Bigi, A., Foresti, E., Koch, M. H. J., Mango, F., Ripamonti, A., and Roveri, N. (1998) X-ray diffraction on cyclically loaded osteons. Calc. Tissue Int., 62, 266–273.

Ascenzi, A. and Bonucci, E. (1972) The shearing properties of single osteons. Anat. Rec., 172, 499–510.

Ascenzi, A. and Bonucci, E. (1968) The compressive properties of single osteons. Anat. Rec., 161, 377–392.

Ascenzi, A. and Bonucci, E. (1967) The tensile properties of single osteons. Anat. Rec., 158, 375–386.

Ascenzi, A. and Bonucci, E. (1964) The ultimate tensile strength of single osteons. Acta Anat., 58, 160–183.

Ascenzi, A., Bonucci, E., Bocciarelli, S. (1965) An electron microscope study of osteon calcification. J. Ultr. Research., 12, 287–303.

Ascenzi, A., Boyde, A., Portigliatti-Barbos, M. and Carando, S. (1987a) Micro-biomechanics vs Macrobiomechanics in cortical bone. A micromechanical investigation of femurs deformed by bending. J. Biomech., 20, 1045–1053.

Ascenzi, A., Improta, S., Portigliatti-Barbos, M. and Carando, S. and Boyde, A. (1987b) Distribution of lamellae in human femoral shafts deformed by bending with inferences on mechanical properties. Bone, 8, 319–325.

Ascenzi, M.-G. (2000) National Science Foundation grant description.

Ascenzi, M.-G. (1999a.) Evidence of macroscopic prestress in human femoral shaft, Abstracts of the XV11th conference of the International Society of Biomechanics, Calgary.

Ascenzi, M.-G. (1999b) A first estimation of prestress in so-called circularly fibered osteonic lamellae, J. Biomech., 32, 935.

Ascenzi, M.-G. (1998a) A first estimate of prestress in so-called circularly fibered osteonic lamellae, Abstracts of the 11th conference of the European Society of Biomechanics, J. Biomech., 31, Suppl. 1, 22.

Ascenzi, M.-G. Benvenuti, A., and Ascenzi, A. (2000) Single osteon micromechanical testing. In: Mechanical testing of bone (An Y. and Draughn R. eds), CRC Press, Boca Raton, Fla.

Bell, G. H. (1956) Bone as a mechanical engineering problem. In: The Biochemestry and Physiology of Bone (Boume G. H. ed) Academic Press, New York.

Bloom, W. and Fawcetts D. (1986) A Textbook of Histology. W. B. Saunders, Philadelphia.

Boume, G. H. (1971) The Biochemistry and Physiology of Bone, Academic Press, New York.

Boyde, A., Bianco, P., Portigliatti-Barbos, M. and Ascenzi, A. (1984) Collagen Orientation in compact bone: 1. A new method for the determination of the proportion of collagen parallel to the plane of compact bone sections. Metab. Bone Dis. & Rel. Res., 5, 299–307.

Burr, D. B., Schaffler, M. B. and Frederickson, R. G. (1988) Composition of the cement line and its possible mechanical role as a local interface in human compact bone. J. Biomech., 21, 939–945.

Cater, W. E. and Carter, D. R. (1989) Bone creep-fatigue damage accumulation. J. Biomech., 22, 625–636.

Carando, S., Portigliatti-Barbos, M., Ascenzi, A. and Boyde, A. (1989) Orientation of collagen in human tibial and fibular shaft and possible correlation with mechanical properties. Bone, 10, 139–142.

Carando, S., Portigliatti-Barbos, M., Ascenzi, A., Riggs, C., and Boyde, A. (1991) Macroscopic shape of, and lamellar distribution within, the upper limb shafts, allowing inferences about mechanical properties. Bone, 12, 265–269.

Carter, D. R., Cater, W. E., Spengler, D. M., and Frankel, V. H. (1981) Acta Orthop. Scand., 52, 481–490.

Carter, D. R. and Hayes, W. C. (1977) Compact bone fatigue damage—I. Residual strength and stiffness. J. Biomech., 10, 325–337.

Carter, D. R. and Hayes, W. C. (1976) Fatigue life of compact bone—I. Effects of stress amplitude, temperature and density. J. Biomech., 9, 27–34.

Carter, D. R., Hayes, W. C. and Schurman, D. J. (1976) Fatigue life of compact bone—II Effects of microstructure and density. J. Biomech., 9, 211–218.

Carter, D. R. and Spengler, D. M. (1978) Mechanical properties and composition of cortical bone. Clin. Orthop., 135, 192–217.

Cook, J. and Gordon, J. E. (1964) A mechanism for the control of crack propagation in all brittle systems. Proc. R. Soc. Lond., Ser. A, 282, 508–520.

Couteau, B., Payan, Y., Lavallée, S. (2000) The mesh-matching algorithm: an automatic 3D mesh generator for finite element structures. J. Biomech., 33, 1005–1009.

Crolet J.-M., Aoubiza, B. and Meunier, A. (1993) Compact bone: numerical simulation of mechanical characteristics. J. Biomech., 26, 677–687.

Currey, J. D. (1969) The relationship between the stiffness and the mineral content of bone. J. Biomech., 2, 477–480.

Currey, J. D. (1964) Three analogies to explain the mechanical properties of bone. Biorheology, 2, 1–10.

Currey, J. D. (1962) Stress concentrations in bone. Quart. J. Microscop. Sci., 103, 111–113.

Currey, J. D. (1959) Differences in tensile strength of bone of different hystological types. J. Anat., 93, 87–95.

Evans, F. G. and Vincentelli, R. (1969) Relation of collagen fiber orientation to some mechanical properties of human cortical bone. J. Biomech., 2, 63–71.

Evans, P. (1978) Relations between torsion properties and histology of adult human compact bone. J. Biomech., 11, 157–165.

Frasca, P., Harper, R. and Katz, J. (1977) Collagen fiber orientation in human secondary osteons. Acta Anat., 98, 1–13. Frasca, P., Harper, R. and Katz, J. (1981) Strain and frequency dependence of shear storage modulus for human single osteons and cortical bone microsamples-size and hydration effects. J. Biomech, 14, 679–690.

Gebhardt, W., (1906) Ueber funktionell wichtige Anordnungsweisen der feineren und gröberen Bauelemente des Wirbeltierknochens. II. Spezieller Teil. 1. Der Bau der Haverssohen Lamellensysteme und seine funktionelle Bedeutung. Arch. Entwickl. Mech Org., 20, 187–322.

Giraud-Guille, M. M. (1988) Twisted plywood architecture of collagen fibrils in human compact bone osteons. Calc. Tissue Int., 42, 167–180.

Gupta, V., and Bergström, J. S. (1998) Compressive failure of rocks by shear faulting. J. of Geoph. Res. 103, 23,875–23,895.

Hazama, H. (1956) Study on torsional strength of the compact substance of human being. J. Kyoto Pref. Med. Univ., 60, 167–184 (Japanese text).

Hert J., Fiala P. and Petrtyl M. (1994) Osteon orientation of the diaphysis of the long bones in man. Bone, 15, 269–277.

Hayes, W. and Carter, D. (1979) Biomechanics of Bone. In: Skeleton Research: An Experimental Approach (D. Simmons and A. Kunin, eds.), Academic Press Inc., New York, 1, 263–299.

Hohling, H. J., Barckhaus, R. H., Krefling, E. R., Althoff, J. and Quint, P. (1990) Collagen mineralization: aspects of the structural relationship between collagen and apatite cristallites. In: Ultrastructure of Skeletal Tissues: Bone and Cartilage in Health and Disease (E. Bonucci and P. M. Morra, eds.), Kluwer Academic Publishers, Boston, 41–62.

Huja, S. S., Hasan, M. S., Pidaparti, R., Turner, C. H., Garetto, L. P. and Burr, D. (1999) Development of a fluorescent light technique for evaluating microdamage in done subjected to fatigue loading. J. Biomech., 32, 1243–1249.

Jepsen, K. J. and Davy, D. T. (1997) Comparison of damage accumulation measures in human cortical bone. J. Biomech., 30, 891–894.

Jepsen, K. J., Davy, D. T. and Krzypow, D. J. (1999) The role of the lamellar interface during torsional yielding of human cortical bone. J. Biomech., 32, 303–310.

Jones, R. M. (1975) Mechanics of Composite Materials. McGraw-Hill, N.Y.

Katz, J. L. and Meunier, A. (1987) The elastic anisotropy of bone. J. Biomech., 20, 1063–1070.

Katz, J. L. and Ukraincik, K. (1971) On the anisotropic elastic properties of hydroxyapatite. J. Biomech., 4, 221–227.

Kleerekoper, M., Villanueva, A. R., Stanciu, J., et al. (1985) The role of three-dimensional trabecular microstructure in the pathogenesis of vertebral compression fractures. Calc. Tissue. Int., 37, 594–597.

Knets, I., Pfafrod, G., Saulgozis, Y., Laizan, Y. and Yanson, K. (1973) Degree of deformation and strength of compact bone tissue during torsion. Polymer Mech., 5,911–918. (Russian text).

Koch, J. C. (1917) The laws of bone architecture. Am. J. Anat., 21, 177–293.

Lakes, R. (1995) On the torsional properties of single osteons, J. Biomech., 28, 1409–1410.

Mah, J. and Hatcher, D. (2000) Imagining trends and applications for the millenium. Orthod. Prod., 1, 14–18.

Marotti, G., Muglia, M. A., Palumbo, C., and Zoffe, D. (1994) The microscopic determinants of bone mechanical properties. Ital. J. Miner. Electrolyte Metab., 8, 167–175.

Martens, M., van Audekercke, R., de Meester, P. and Mulier, J. (1980) The mechanical characteristics of the long bones of the lower extremity in torsional loading. J. Biomech., 13, 667–676.

Meunier, A. (1999) Personal communication.

Miller, G. and Piotrowski, G. (1974) A brief note on the variability of the torsional strength of paired bones. J. Biomechanics, 7, 247–248.

Moore D. and McCabe G. (1989) Introduction to the practice of statistics. W. H. Freeman and Co., New York.

Moreland, M. (1980) Morphological effects of torsion applied to growing bone. J. Bone Jt. Surg., 62-B, 230–237.

Narayanan R. and Roberts T. (I 991) Structures Subjected to Repeated Loading. Stability and Strength, Elsevier, London.

Petersen, H. (1930) Die Organe des Skeletsystems. In: Handhuch der mikroskopischen Anatomie des Menshen (Mollendorff (v.), W. ed.), Springer, Berlin, 521–678.

Pfafrod, G., Saulgozis, Y., Knets, I., Saulgozis, Y. and Yanson, K. (1972) Experimental determination of the shear modulus of compact bone. Polymer Mech., 4, 697–705. (Russian text).

Philipson, B. (1965) Composition of cement lines in bone. J. Histochem. Cytochem., 13, 270–281.

Pidaparti, R. and Burr D. (1992) Collagen fiber orientation and geometry effects on the mechanical properties of secondary osteons. J. Biomech., 25, 869–880.

Piekarski, K. (1970) Fracture of bone. J. of Appl. Physics, 41, 215–223.

Portigliatti-Barbos, M., Bianco, P. and Ascenzi, A. (1983) Distribution of osteonic and interstitial components in the human femoral shaft with reference to structure, calcification, and mechanical properties. Acta Anat., 15, 178–186.

Portigliatti-Barbos, M., Bianco, P., Ascenzi, A. and Boyde, A. (1984) Collagen orientation in compact bone: II. Distribution of lamellae in the whole of the human femoral shaft with reference to its mechanical properties. Metab. Bone Dis. & Rel. Res., 5, 309–315.

Portigliatti-Barbos, M., Carando, S., Ascenzi, A. and Boyde, A. (1987) On the structural symmetry of human femurs, Bone, 8, 165–169.

Rauber, A. (1873) Elasticitat and Festigkeit der Knochen. Leipzig, Wilhelm Engelmann.

Rho, J. Y., Zioupos, P., Currey, J. D., and Pharr, G. M. (1999) Variations in the individual thick lamellar properties within osteons by nanoindentation, Bone, 25, 295–300.

Riggs, C. M., Lanyon, L. E., and Boyde, A. (1993a) Functional associations between collagen fibre orientation and locomotor strain direction in cortical bone of the equine radius, Anat. Embryol., 187, 231–238.

Riggs, C. M., Vaughan, L. C., Evans, G. P., Lanyon, L. E. and Boyde, A. (1993b) Mechanical implications of collagen fibre orientation in cortical bone of the equine radius, Anat. Embryol., 187, 239–248.

Sasaki N. (2000) Viscoelastic properties of bone and testing methods. In: Mechanical testing of bone (An Y. and Draughn R. eds), CRC Press, Boca Raton, Fla.

Schaffler, M., Burr, D. B. and Frederickson, R. G. (1987) Morphology of the osteonal cement line in human bone. Anat. Rec., 217, 223–228.

Shiga, T., Ogawa, J., Shibata, A. and Shibuya, J. (1970) The dynamic properties of reinforced concrete frames.

Simkin, A., and Robin, G. (1974) Fracture formation in differing collagen fiber pattern of compact bone. J. Biomech., 7, 183–188.

Timoshenko, S., and Young, D. H. (1962) Elements of Strength of Materials. Van Nostrand, Princeton.

Vincentelli, R. and Evans, F. G. (1971) Relations among mechanical properties, collagen fibers, and calcification in adult human cortical bone. J. Biomech., 4, 193–201.

Vinson, J. R. (1993) The Behavior of Shells Composed of Isotropic and Composite Materials. Kluwer Academic Publishers, Boston.

Wickramasinghe, S. N. (1975) Human Bone Marrow. Blackwell Scientific Publications, Philadelphia.

Ziv, V., Wagner, M. D., and Weiner, S. (1996) Microstructure-microhardness relations in parallel-fibered and lamellar bone. Bone, 19, 417–428.

Zysset, P. K., Guo X. E., Hoffler C. E., Moore K. E., and Goldstein S. (1999) Elastic modulus and hardness of cortical and trabecular bone lamellae measured by nanoindentation in the human femur. J. Biomech., 32, 1005–1012.

I claim:

1. A system for modeling macrostructural characteristics of a bone comprising:
a first hierarchical order comprising at least one macroscopic region of the bone,
a second hierarchical order comprising at least one empirically-derived nonhomogeneous second order component representing one or more osteons, trabeculae, or lamellae within the macroscopic region, and
a mechanical property correlated to each of the second order components,
wherein a mechanical property of the first hierarchical order region is determined based on the mechanical properties of the second order components.

2. A system as in claim 1, wherein the bone is compact bone or cancellous bone.

3. A system as in claim 1, wherein the mechanical property is selected from the group consisting of tension, compression, shear, bending, torsion, prestress, pinching, and cement line slippage.

4. A system as in claim 1, further comprising:
a third hierarchical order comprising at least one third order component representing one or more collagen bundles, hydroxyapatite crystallites, mucopolysaccharides, or combinations thereof corresponding to one or more regions of the second order components; and
a mechanical property correlated to each of the third order components, wherein the mechanical property of each of the second order components is determined based on the mechanical properties of the third order components.

5. A system as in claim 4, wherein the collagen bundles are randomly distributed transversely to an orientation of at least one of the second order components.

6. A system as in claim 1, wherein at least one of the second order components is anisotropic.

7. A system as in claim 1, wherein:
an external force is applied to the macroscopic region of the bone; and
a response to the external force is determined based on the mechanical properties of the second order components.

8. A system as in claim 1, wherein the mechanical properties of the second order components are assigned based on a plurality of experimental determinations.

9. A system as in claim 1, further comprising:
a plurality of subject bones of a specified type;
wherein a plurality of samples is selected;
one or more mechanical properties of at least one second order component of each sample is evaluated; and
the evaluations are aggregated to determine the mechanical properties of the second order components.

10. A system as in claim 9, wherein the aggregated evaluations are collected in a database of mechanical properties for the subject bone of the specified type.

11. A system as in claim 9, wherein:
the mechanical properties of the second order components are selected from the group consisting of torsional stiffness, angle-of-twist, and torque;
each of the samples are subjected to monotonic and cyclic torsion tests to produce data on torque and angle-of-twist; and
the mechanical properties of the second order components of the selected bone are determined based on a torque vs. angle-of-twist curve of the samples based on the collected data.

12. A system as in claim 9, wherein:
the mechanical properties of the second order components are selected from tension, compression, shear, bending, and torsion;
each of the samples is subjected to tests to produce data on stress and strain; and
the mechanical properties of the second order components of the selected bone are determined based on a stress-strain curve of the samples based on the data.

13. A system as in claim 4, wherein the mechanical properties of each of the second order components vary in dependence on orientation directions of the third order components.

14. A system as in claim 13, wherein the orientation directions of the third order components are assigned based on experimental determinations.

15. A system as in claim 14, wherein orientation directions of the third order components of the selected bone that is modeled are determined based on the orientation directions of the third order components observed in a subject bone of a specified type.

16. A system as in claim 13, wherein:
the second order components comprise alternate, extinct, and bright osteons, classified by their appearance in cross section under circularly polarized light;
the alternate osteons comprise extinct lamellae layered between bright lamellae;
the extinct osteons comprise extinct lamellae;
collagen bundles in each of the extinct lamellae are oriented in alternating layers with orientation directions of about 82° and −82° with respect to the osteon axis; and
collagen bundles in bright lamellae are oriented in successive layers with orientation directions of about −61.5°, −41°, −20.5°, 0°, 20.5°, 41°, and 61.5° with respect to the osteon axis.

17. A system as in claim 4, wherein:
boundary conditions for relative ability to move under loading are assigned to the third order components of the selected bone; and
deformation or fractures are calculated using mechanical properties assigned to the third order components, the force acting on the selected bone, and the boundary conditions of the third order components of the selected bone.

18. A system as in claim 4, wherein a relative amount of the third order components depends on degree of calcification of the second order components.

19. A system as in claim 18, wherein the degree of calcification of the second order components is assigned based on experimental determinations.

20. A system as in claim 16, wherein distribution of alternate osteons, extinct lamellae, and bright lamellae depends on experimental determinations.

21. A system as in claim 1, wherein the second order components comprise voids representing canaliculae, lacunae, or combinations thereof.

22. A method of producing a model of a bone comprising the steps of:
  a) specifying a first order macroscopic region of a selected bone;
  b) dividing the macroscopic region into a finite number of elements of second hierarchical order, each element representing an empirically-derived nonhomogeneous second order component comprising one or more osteons, trabeculae, or lamellae;
  c) assigning a mechanical property to each second order component; and
  d) determining a mechanical property of the first order macroscopic region of the selected bone based on the mechanical properties of the second order components.

23. A method of claim 22, further comprising:
  dividing each second order component into a finite number of elements, each element representing a third order component comprising one or more collagen bundles, hydroxyapatite crystallites, mucopolysaccharides, or combinations thereof; and
  assigning a mechanical property to each third order component, wherein the mechanical property of each of the second order components is assigned based on the mechanical properties of the third order components.

24. A method of claim 22, wherein the collagen bundles are randomly distributed transversely to an orientation of at least one of the second order components.

25. A method of claim 22, wherein at least one of the second order components is anisotropic.

26. A method of claim 22, further comprising:
  applying an external force to the macroscopic region of the bone; and
  determining a response to the external force based on the mechanical properties of the second order components.

27. A method of claim 22, wherein the mechanical properties of the second order components are assigned based on a plurality of experimental determinations.

28. A method of claim 27, wherein the experimental determinations comprise the steps of:
  selecting a plurality of subject bones of a specified type;
  selecting a plurality of samples;
  evaluating one or more mechanical properties of at least one second order component of each sample; and
  aggregating the evaluations.

29. A method of claim 28, wherein the experimental determination further comprises the steps of:
  repeating the experimental determination steps for subject bones of different types;
  and compiling a database of representative mechanical properties of each type of subject bone based on the aggregated evaluations.

30. A method of claim 28, wherein the experimental determination further comprises:
  performing monotonic and cyclic torsion tests on each of the samples;
  collecting data on torque and angle-of-twist of each of the samples;
  determining a torque vs. angle-of-twist curve for each of the samples based on the collected data; and
  determining the mechanical properties of the second order components of the selected bone based on the torque vs. angle-of-twist curve of the samples.

31. A method of claim 30, wherein the step of determining the mechanical property of the second order components of the selected bone comprises the step of examining the torque vs. angle-of-twist curve to determine if a change of stiffness occurs.

32. A method of claim 28, wherein the mechanical properties are selected from tension, compression, shear, bending, and torsion on each of the samples, the experimental determinations further comprise:
  generating data on stress and strain of each of the samples based on testing the selected mechanical properties;
  determining a stress-strain curve of the subject bone based on the generated data; and
  determining the mechanical properties of the second order components of the selected bone based on the stress-strain curve of the samples.

33. A method of claim 32, wherein the mechanical properties are further selected from the group consisting of Young's modulus, Poisson's ratio, and yield strength.

34. A method of claim 28, wherein the experimental determination further comprises the steps of:
  measuring dimensions of samples before and after a step of cutting the subject bone into samples, and before performing a mechanical test on the samples;
  performing a mechanical test on the samples;
  determining a change in the dimensions of each sample; and
  determining a prestress in each sample based on the change in the dimensions of the samples.

35. A method of claim 23, further comprising the step of modifying the mechanical properties of each of the second order components based on orientation directions of the third order components.

36. A method of claim 35, wherein the orientation directions of the third order components are assigned based on experimental determinations.

37. A method of claim 36, wherein the experimental determination further comprises the steps of:
  selecting a subject bone of a specified type;
  observing orientation directions of third order components of the subject bone;
  determining orientation directions of the third order components of the selected bone based on the orientation directions of the third order components of the subject bone.

38. A method of claim 35, wherein:
  the second order components comprise alternate, extinct, and bright osteons, classified by their appearance in cross section under circularly polarized light;
  the alternate osteons comprise extinct lamellae layered between bright lamellae,
  the extinct osteons comprise extinct lamellae, and
  wherein the method further comprises the steps of
  orienting the collagen bundles in each of the extinct lamellae by alternating layers of collagen bundles with orientation directions of about 82° and −82° with respect to the osteon axis, and
  orienting the collagen bundles in bright lamellac in successive layers with orientation directions in sequence of about −61.5°, −41°, −20.5°, 0°, 20.5°, 41°, and 61.5° with respect to the osteon axis.

39. A method of claim 23, further comprising the step of positioning the third order components randomly within a transverse plane of each of the second order components, wherein the transverse plane is positioned transverse to an axis of the corresponding second order component.

40. A method of claim 23, further comprising the steps of:
assigning a force acting on the selected bone;
assigning boundary conditions for relative ability to move under loading to the third order components of the selected bone; and
computing deformation or fractures of the selected bone using the mechanical properties assigned to the third order components, the force acting on the selected bone, and the boundary conditions of the third order components of the selected bone.

41. A method of claim 40, further comprising the step of determining fracture lines within the selected bone based on locations of cement lines that are formed between the second order components.

42. A method of claim 40, wherein the boundary conditions of the third order components are assigned based on experimental determinations.

43. A method of claim 40, wherein the boundary conditions of the third order components located at an interface between the second order components are each specified as having freedom of movement under loading.

44. A method of claim 40, wherein the boundary conditions of at least one of the third order components are specified as having freedom of movement under loading.

45. A method of claim 28, wherein the second order sample is an osteon.

46. A method of claim 23, wherein a relative amount of the third order components depends on degree of calcification of the second order components.

47. A method of claim 46, wherein the degree of calcification of the second order components is assigned based on experimental determinations.

48. A method of claim 38, wherein distribution of alternate osteons, extinct lamellae, and bright lamellae depends on experimental determinations.

49. A method of claim 22, wherein the second order components comprise voids representing canaliculae, lacunae, or combinations thereof.

50. A method of claim 21, wherein the macroscopic region is represented by a three-dimensional image, which is divided to provide the finite elements.

* * * * *

UNITED STATES PATENT AND TRADEMARK OFFICE
CERTIFICATE OF CORRECTION

PATENT NO.      : 7,124,067 B2
APPLICATION NO. : 09/981684
DATED           : October 17, 2006
INVENTOR(S)     : Maria-Grazia Ascenzi It is certified that error appears in the above-identified patent and that said Letters Patent is hereby corrected as shown below:

Amendments to the Specification:

Please replace the paragraph at col. 4, lines 21-24 with the following amended paragraph:

FIG. 1. A schematic representation of the upper third of the tibia; i.c.s. and o.c.s. stand for inner and outer circumferential systems, respectively. Both compact and cancellous bone are represented (from Bonucci, 2000, Basic composition and structure of bone. In: Mechanical Testing of Bone (An Y. and Draughn R. eds.) pp. 3-21, CRC Press, Boca Raton, Florida).

Please replace the paragraph at col. 4, lines 25-32 with the following amended paragraph:

FIGS. 2(*a*) and (*b*). (a) Diagram of a diaphysis sector of cortical long bone. The osteons or haversian system (HA) are located between the outer OL and inner IL circumferential lamellae. The osteonic lamellae are disposed cylindrically around the haversian canal (HC) (from Bouligand et al., (1985) Spatial organization of collagen fibrils in skeletal tissues: analogies with liquid crystals. In: Bairati A. Garrone R (eds.) Biology of invertebrate and lower vertebrate collagens. Plenum Publishing Corp.). (b-d) Cross-sectioned osteons as seen (b) under a light microscope; (c) in a microradiograph; and (d) under the polarizing microscope (from Bonucci, 2000).

Figure 3A:
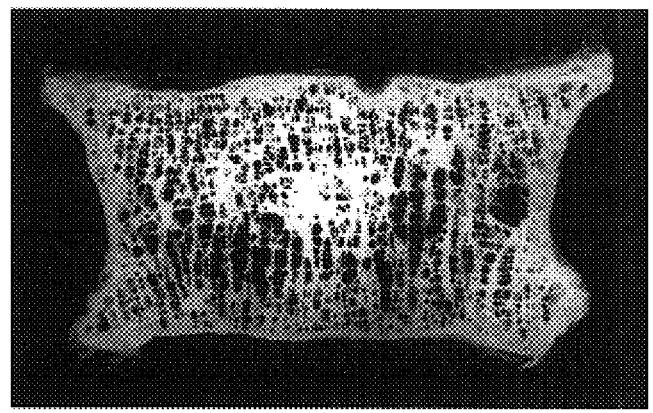
FIGS. 3(a) and (b). (a) Section of the body of a lumbar vertebra showing vertical and horizontal trabeculae. The upper and lower surfaces correspond to articular cartilage. (b) Section of half of tibia's upper third. The cancellous bone of the metaphysis consists of comparatively think vertical trabeculae connected by thin trabeculae.
Figure 3B:
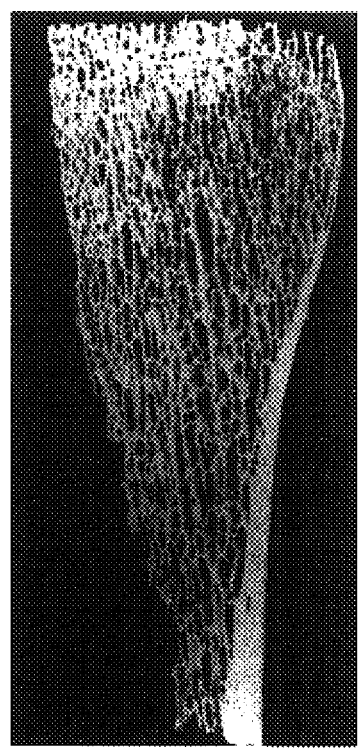

Please replace the paragraph at col. 4, lines 33-38 with the following amended paragraph:

FIGS. 3(*a*) and (*b*). (a) Section of the body of a lumbar vertebra showing vertical and horizontal trabeculae. The upper and lower surfaces correspond to articular cartilage (from Bonucci, 2000). (b) Section of half of tibia's upper third. The cancellous bone of the metaphysis consists of comparatively think vertical trabeculae connected by thin trabeculae (from Bonucci, 2000).

Please replace the paragraph at col. 4, lines 49-51 with the following amended paragraph:

FIGS. 6(*a*)-(*c*). (a) Types of pure forces;[[.]] (b) Definition of stress on an area on which the force is constant;[[.]] (c) Definition of unidirectional strain for D much smaller than L (from Evans F. G., Mechanical Properties of Bone, Thomas, Springfield, 1973).

UNITED STATES PATENT AND TRADEMARK OFFICE
CERTIFICATE OF CORRECTION

Figure 7A:
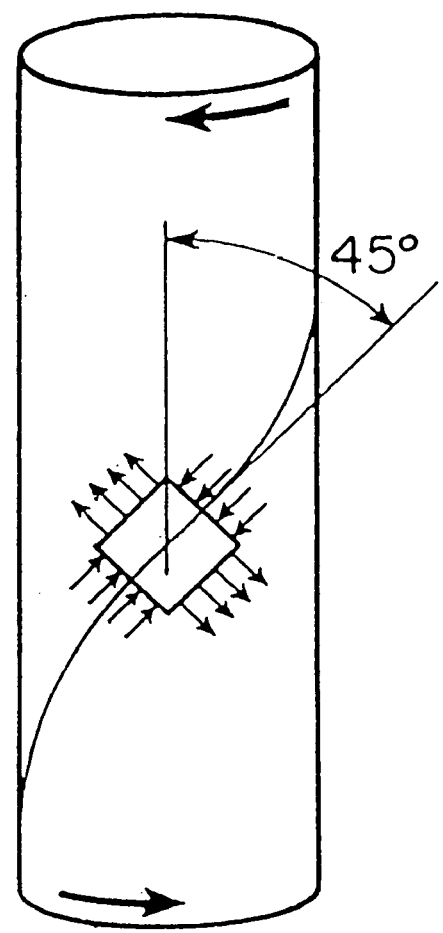
FIGS. 7(a) and (b). (a) Tensile and compressive stress distribution during torsion in a material, such as macroscopic bone, which is weaker in tension than in shear. (b) Shearing stress on the cross section of a specimen subjected to torsion. The arrows' length indicates the magnitude of the shearing stress, which progressively increases from the center to the periphery of the specimen.
Figure 7B:
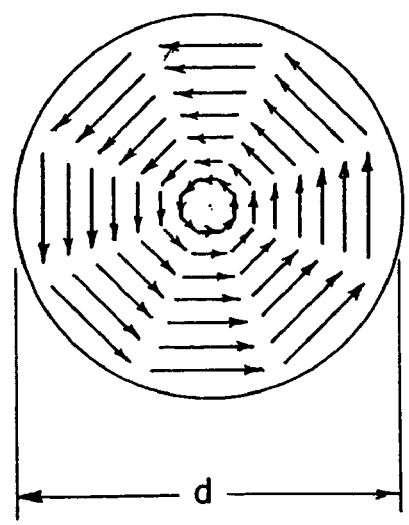

PATENT NO.         : 7,124,067 B2
APPLICATION NO.    : 09/981684
DATED              : October 17, 2006
INVENTOR(S)        : Maria-Grazia Ascenzi It is certified that error appears in the above-identified patent and that said Letters Patent is hereby corrected as shown below:

Please replace the paragraph at col. 4, lines 52-58 with the following amended paragraph:

FIGS. 7(*a*) and (*b*). (a) Tensile and compressive stress distribution during torsion in a material, such as macroscopic bone, which is weaker in tension than in shear;[[.]] (b) Shearing stress on the cross section of a specimen subjected to torsion. The arrows' length indicates the magnitude of the shearing stress, which progressively increases from the center to the periphery of the specimen (from Evans, 1973).

Please replace the paragraph at col. 5, lines 12-23 with the following amended paragraph:

FIGS. 9(*a*)-(*c*). (a) The osteonic lamellar model is a laminate, which consists of fiber-reinforced unidirectional laminae. (b) The interstitial lamellar model is a portion of the osteonic lamellar model. The figure shows three thin laminae (lamellae) and a thick lamina (portion of cement line) (from Crolet, J.M., Aoubiza, B., and Meunier, A., Compact bone: numerical simulation of mechanical characteristics. J. Biomechanics. (26):677-687. 1993). (c) On a small laminar element of constant thickness, the principal material axes are labeled 1, 2, and 3. Direction 1 is parallel and direction 2 is perpendicular to the fibers. Direction 3 is the radial direction perpendicular to the page. Circumferential and axial directions are labeled $\Theta$ and z. The angle between the circumferential direction and direction 1 is called $\gamma$ (from Ascenzi, M.-G. (1999) A first estimation of prestress in so-called circularly fibered osteonic lamellae, J. Biomechanics. (32): 935-942).

Please replace the paragraph at col. 5, lines 24-25 with the following amended paragraph:

FIG. 10. Shows a device for subjecting bone to torsional cyclical loading (from Ascenzi, A. Baschieri, P. Benvenuti, A. (1994) The torsional properties of single selected osteons. J. Biomechanics, 27(7): 875-884).

Please replace the paragraph at col. 5, lines 26-31 with the following amended paragraph:

FIG. 11. A schematic diagram of a device for subjecting bone to torsional cyclical loading, where (1) is a rotational axis with jaws; (2) and (3) are hard metal wedges of a pendulum loading system; (4) is a wheel around which a tungsten thread loaded with weights is attached; (5) is the axis of the pendulum; and (6) is a mirror (from Ascenzi, A. Baschieri, P. Benvenuti, A. (1994) The torsional properties of single selected osteons. J. Biomechanics, 27(7): 875-884).

UNITED STATES PATENT AND TRADEMARK OFFICE
CERTIFICATE OF CORRECTION

| | | |
|---|---|---|
| PATENT NO. | : 7,124,067 B2 | |
| APPLICATION NO. | : 09/981684 | |
| DATED | : October 17, 2006 | |
| INVENTOR(S) | : Maria-Grazia Ascenzi | |

It is certified that error appears in the above-identified patent and that said Letters Patent is hereby corrected as shown below:

Please replace the paragraph at col. 5, lines 35-37 with the following amended paragraph:

FIG. 13. A diagram that shows that around each osteon sample, a trapezoid was cut with a blade under a stereo microscope (from Ascenzi, M.-G, Ascenzi, A., Burghammer, M., Panzavolta, S., Benvenuti, A. and Bigi, A. (2003) Structural differences between "dark" and "bright" isolated human osteonic lamellae, J. Structural Biology, 141, 22-33).

Figure 14:
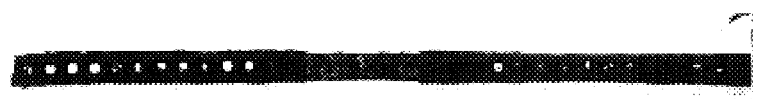
FIG. 14. A diagram that shows that after isolation, each lamellar sample was carefully straightened to a ribbon-like shape.

Please replace the paragraph at col. 5, lines 38-40 with the following amended paragraph:

FIG. 14. A diagram that shows that after isolation, each lamellar sample was carefully straightened to a ribbon-like shape (from Ascenzi, A. Benvenuti, A. Bonucci, E. (1982) The tensile properties of single osteonic lamellae: technical problems and preliminary results. J. Biomechanics, 15(1): 29-37).

Figure 15:
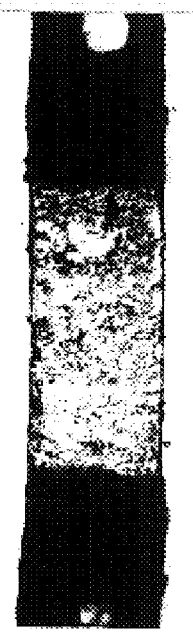
FIG. 15. A larger view of the lamella described in FIG. 14.

Please replace the paragraph at col. 5, line 41 with the following amended paragraph:

FIG. 15. A larger view of the lamella described in FIG. 14 (from Ascenzi, A. Benvenuti, A. Bonucci, E. (1982) The tensile properties of single osteonic lamellae: technical problems and preliminary results. J. Biomechanics, 15(l): 29-37).

Figure 16:
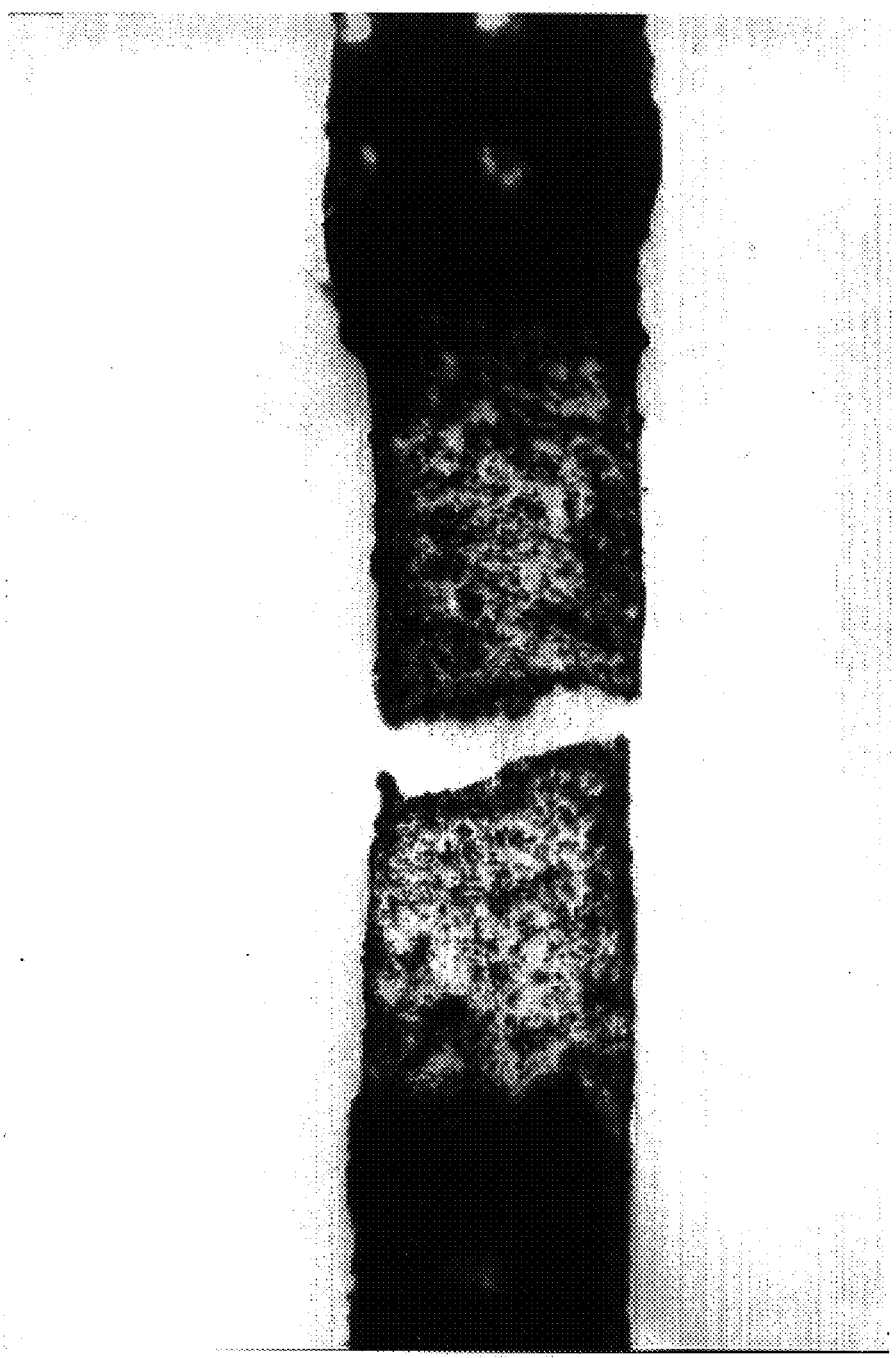
FIG. 16. A lamella after tensional testing.
Figure 17:
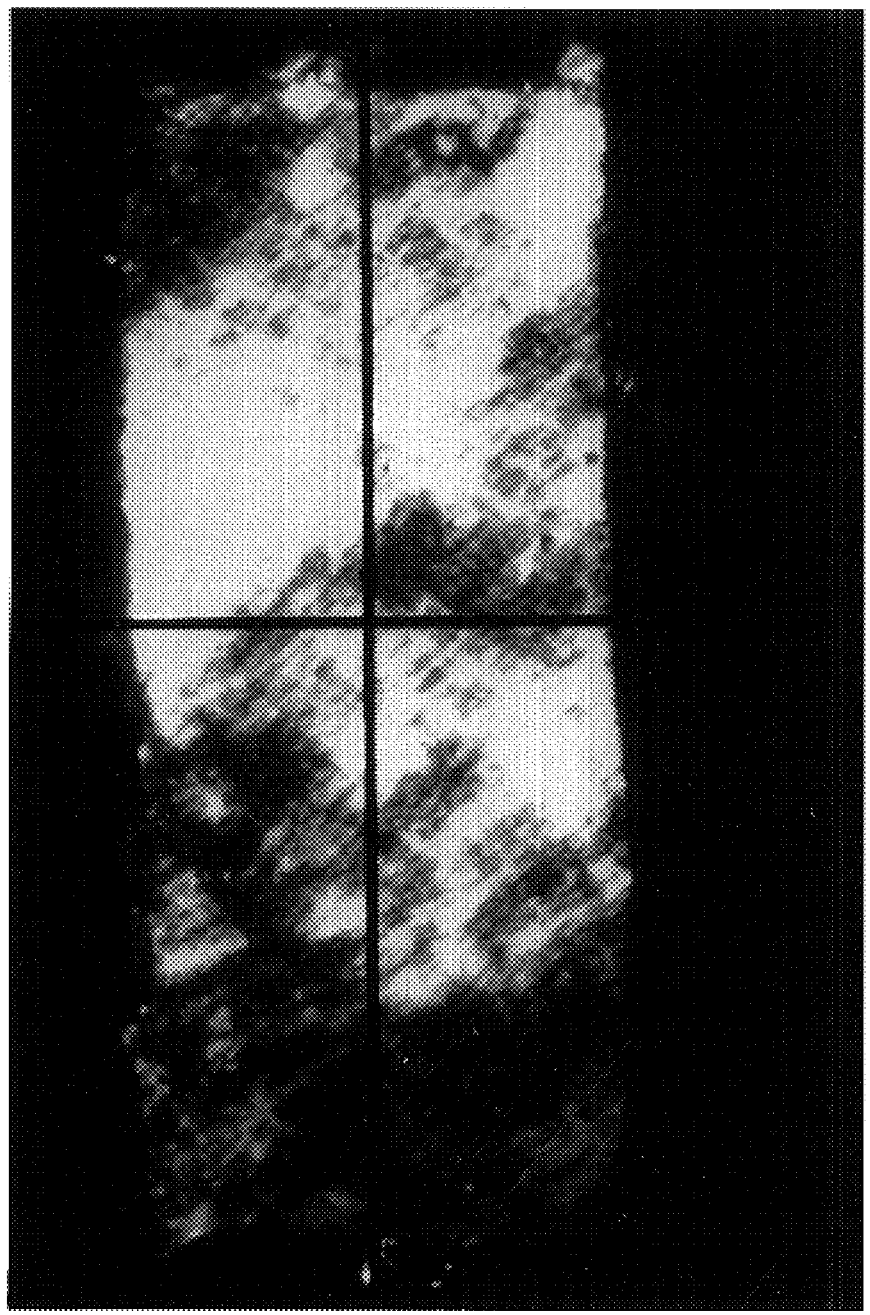
FIG. 17. Collagen bundles of bright lamella under polarized microscope.
Figure 18:
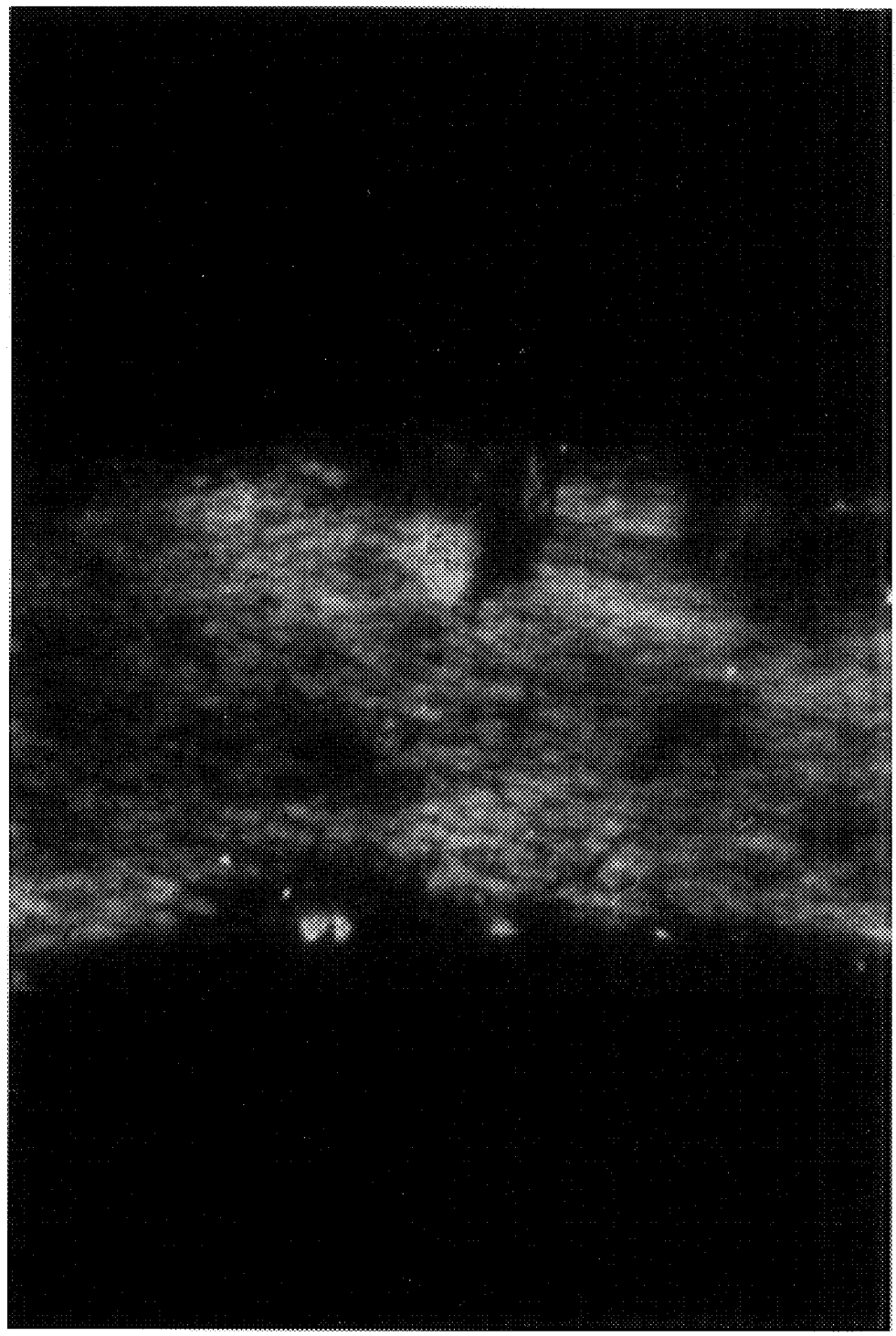
FIG. 18. Collagen bundles of bright lamella under polarized microscope.
Figure 19:
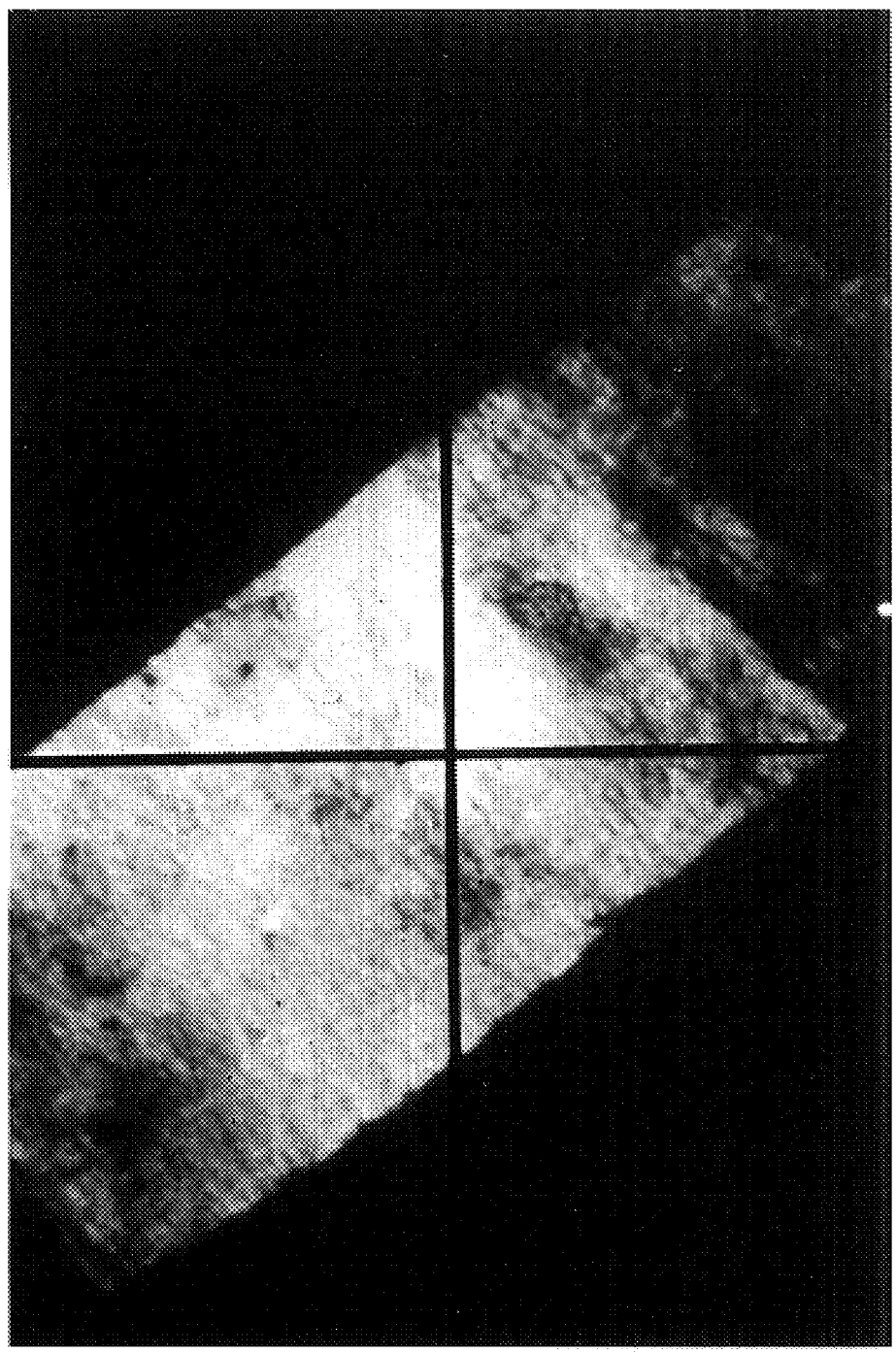
FIG. 19. Collagen bundles of extinct lamella under polarized microscope. Bundles are parallel to the osteon axis when embedded in bone.
Figure 20A:
FIGS. 20(a)–(h). Isolated and flattened bright lamella under the confocal microscope. From border to center, the collagen bundles go from oblique to vertical.
Figure 20B:
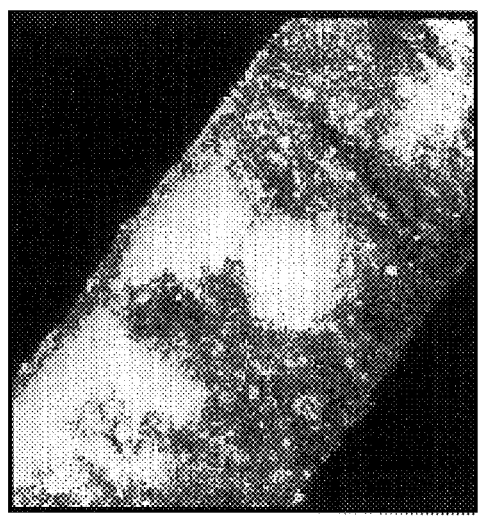
Figure 20C:
Figure 20D:
Figure 20E:
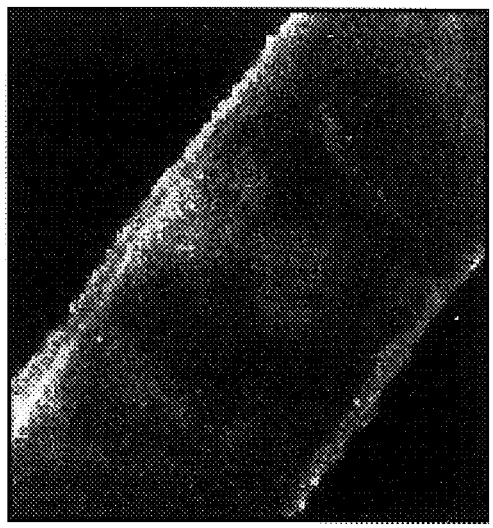
Figure 20F:
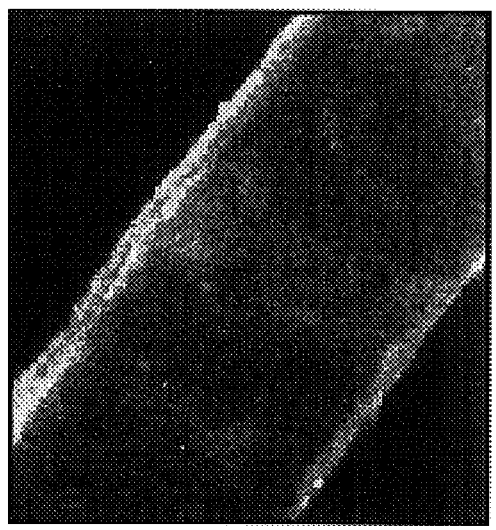
Figure 20G:
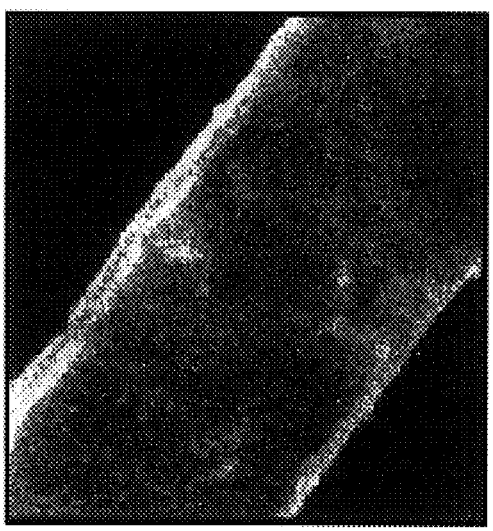
Figure 20H:
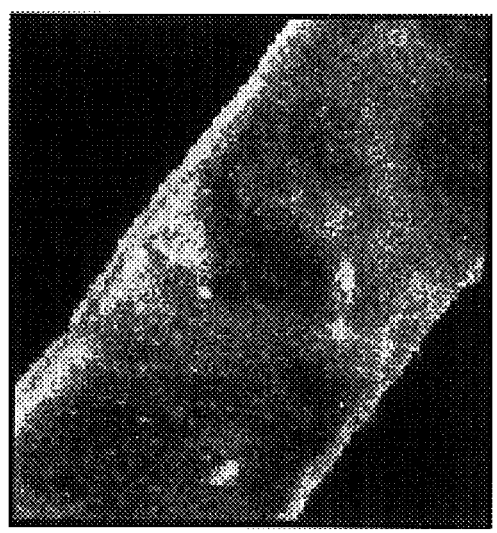
Figure 21A:
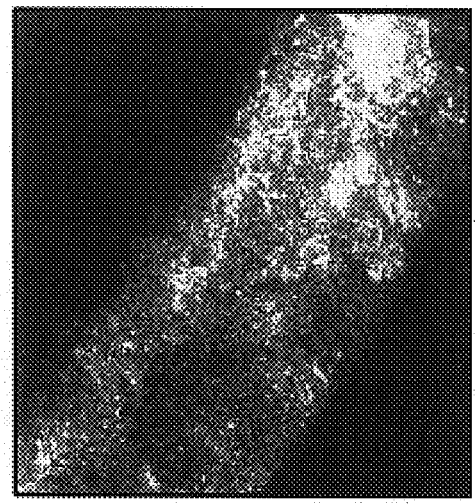
FIGS. 21(a)–(g). Isolated and flattened extinct lamella under the confocal microscope. From one border to the other, the collagen bundles are parallel to the osteonal axis.
Figure 21B:
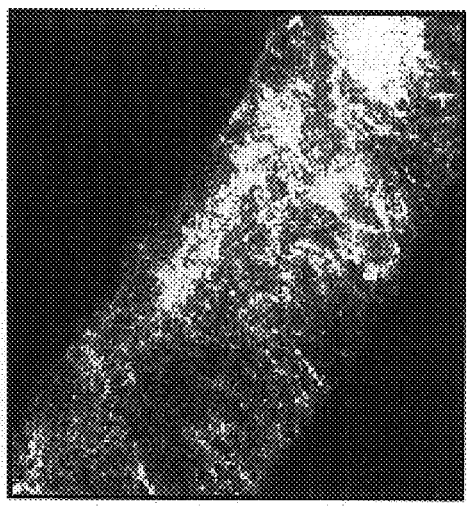
Figure 21C:
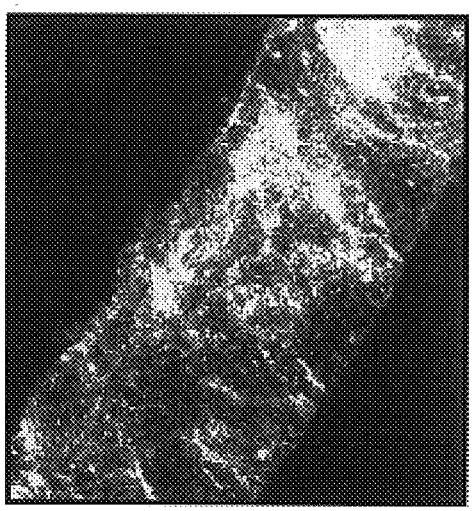
Figure 21D:
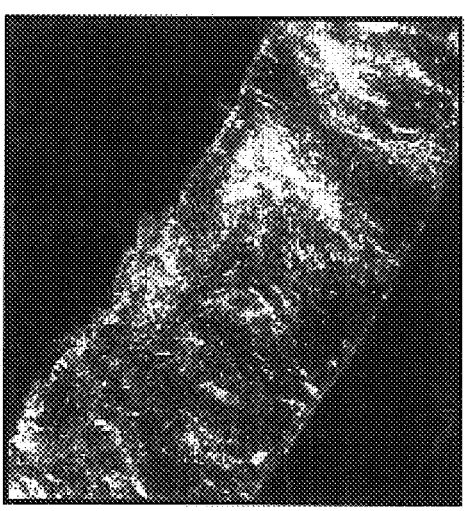
Figure 21E:
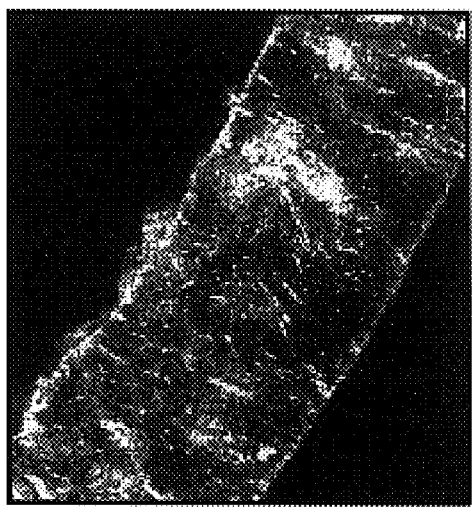
Figure 21F:
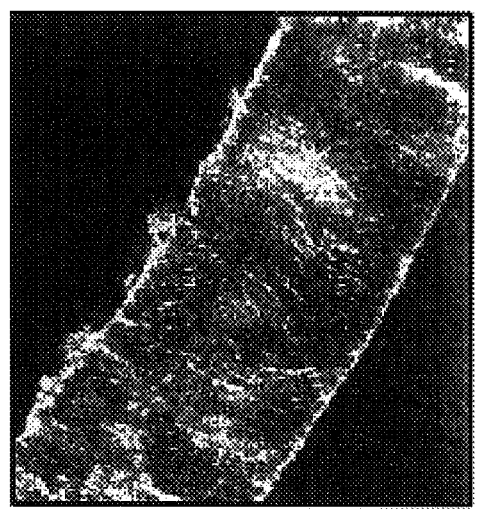
Figure 21G:
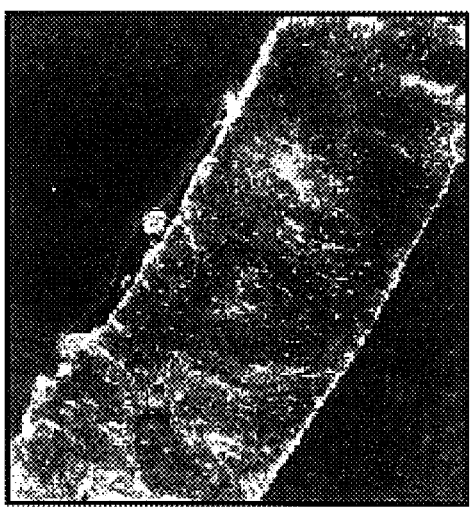

Please replace the paragraph at col. 5, line 42 with the following amended paragraph:

FIG. 16. A lamella after tensional testing (from Ascenzi, A, Benvenuti, A, Bonucci, E. (1982) The tensile properties of single osteonic lamellae: technical problems and preliminary results. J. Biomechanics, 15(1): 29-37).

Please replace the paragraph at col. 5, lines 50-52 with the following amended paragraph:

FIGS. 20 (*a*)-(*h*). Isolated and flattened bright lamella under the confocal microscope. From border to center, the collagen bundles go from oblique to vertical (from Ascenzi, M.-G, Ascenzi, A., Burghammer, M., Panzavolta, S., Benvenuti, A. and Bigi, A. (2003) Structural differences between "dark" and "bright" isolated human osteonic lamellae. J. Structural Biology, 141, 22-33).

UNITED STATES PATENT AND TRADEMARK OFFICE
CERTIFICATE OF CORRECTION

PATENT NO.      : 7,124,067 B2
APPLICATION NO. : 09/981684
DATED           : October 17, 2006
INVENTOR(S)     : Maria-Grazia Ascenzi It is certified that error appears in the above-identified patent and that said Letters Patent is hereby corrected as shown below:

Please replace the paragraph at col. 5, lines 53-55 with the following amended paragraph:

FIGS. 21 (*a*)-(*g*). Isolated and flattened extinct lamella under the confocal microscope. From one border to the other, the collagen bundles are parallel to the osteonal axis (from Ascenzi, M.-G, Ascenzi, A., Burghammer, M., Panzavolta, S., Benvenuti, A. and Bigi, A. (2003) Structural differences between "dark" and "bright" isolated human osteonic lamellae. J. Structural Biology, 141, 22-33).

Signed and Sealed this

Tenth Day of July, 2007

JON W. DUDAS
*Director of the United States Patent and Trademark Office*